(12) United States Patent
Owen et al.

(10) Patent No.: US 8,077,305 B2
(45) Date of Patent: Dec. 13, 2011

(54) IMAGING SEMICONDUCTOR STRUCTURES USING SOLID STATE ILLUMINATION

(76) Inventors: Mark D. Owen, Beaverton, OR (US); Francois Vlach, Portland, OR (US); Steven J. Olson, Portland, OR (US)

( * ) Notice: Subject to any disclaimer, the term of this patent is extended or adjusted under 35 U.S.C. 154(b) by 0 days.

(21) Appl. No.: 11/109,903

(22) Filed: Apr. 19, 2005

(65) Prior Publication Data

US 2005/0231713 A1    Oct. 20, 2005

Related U.S. Application Data

(60) Provisional application No. 60/563,856, filed on Apr. 19, 2004.

(51) Int. Cl.
*G01N 21/00* (2006.01)

(52) U.S. Cl. ..................................... 356/237.1

(58) Field of Classification Search ..... 356/237.2–237.5
See application file for complete search history.

(56) References Cited

U.S. PATENT DOCUMENTS

| | | | |
|---|---|---|---|
| 3,586,959 A | 6/1971 | Eccles et al. | |
| 3,936,686 A | 2/1976 | Moore | |
| 4,011,575 A | 3/1977 | Groves | |
| 4,118,873 A | 10/1978 | Rothchild | |
| 4,435,732 A | 3/1984 | Hyatt | |
| 4,530,040 A | 7/1985 | Petterson | |
| 4,544,642 A | 10/1985 | Maeda et al. | |
| 4,595,289 A * | 6/1986 | Feldman et al. | 356/237.5 |
| 4,680,644 A | 7/1987 | Shirato et al. | |
| 4,684,801 A | 8/1987 | Carroll et al. | |
| 4,685,139 A * | 8/1987 | Masuda et al. | 356/430 |
| 4,734,714 A | 3/1988 | Takasu et al. | |
| 5,003,357 A | 3/1991 | Kim et al. | |
| 5,018,853 A * | 5/1991 | Hechel et al. | 356/155 |
| 5,032,734 A * | 7/1991 | Orazio et al. | 250/559.46 |
| 5,150,623 A | 9/1992 | Woods | |
| 5,195,102 A | 3/1993 | McLean et al. | |
| 5,296,724 A | 3/1994 | Ogata et al. | |
| 5,397,867 A | 3/1995 | Demeo | |
| 5,418,384 A | 5/1995 | Yamana et al. | |
| 5,424,544 A | 6/1995 | Shelton et al. | |
| 5,436,710 A | 7/1995 | Uchiyama | |
| 5,449,926 A | 9/1995 | Holm et al. | |
| 5,490,049 A | 2/1996 | Montalan et al. | |
| 5,522,225 A | 6/1996 | Eskandari | |
| 5,554,849 A | 9/1996 | Gates | |

(Continued)

FOREIGN PATENT DOCUMENTS

DE    8815418    2/1989

(Continued)

OTHER PUBLICATIONS

PCT International Search Report and Written Opinion dated Jun. 7, 2006 for international Application No. PCT/US04/36046, filed Oct. 29, 2004, 6 pages.

(Continued)

*Primary Examiner* — Gregory J Toatley
*Assistant Examiner* — Juan D Valentin
(74) *Attorney, Agent, or Firm* — Ganz Law, P.C.

(57) ABSTRACT

The invention consists of a camera, light sources, lenses and software algorithms that are used to image and inspect semiconductor structures, including through infrared radiation. The use of various configurations of solid state lighting and software algorithms enhances the imaging and inspection.

38 Claims, 19 Drawing Sheets

U.S. PATENT DOCUMENTS

| | | | |
|---|---|---|---|
| 5,555,038 | A | 9/1996 | Conway |
| 5,623,510 | A | 4/1997 | Hamilton et al. |
| 5,632,551 | A | 5/1997 | Roney et al. |
| 5,660,461 | A | 8/1997 | Ignatius et al. |
| 5,698,866 | A | 12/1997 | Doiron et al. |
| 5,715,270 | A | 2/1998 | Zediker et al. |
| 5,719,589 | A | 2/1998 | Norman et al. |
| 5,777,729 | A | 7/1998 | Aiyer et al. |
| 5,783,909 | A | 7/1998 | Hochstein |
| 5,806,965 | A | 9/1998 | Deese |
| 5,857,767 | A | 1/1999 | Hochstein |
| 5,877,899 | A | 3/1999 | Stern et al. |
| 5,880,828 | A * | 3/1999 | Nakamura et al. ......... 356/237.5 |
| 5,892,579 | A * | 4/1999 | Elyasaf et al. ............. 356/237.4 |
| 5,910,706 | A | 6/1999 | Stevens et al. |
| 5,936,353 | A | 8/1999 | Triner et al. |
| 6,033,087 | A | 3/2000 | Shozo et al. |
| 6,058,012 | A | 5/2000 | Cooper et al. |
| 6,088,185 | A | 7/2000 | Ratliff et al. |
| 6,118,383 | A | 9/2000 | Hegyi |
| 6,141,040 | A * | 10/2000 | Toh ............................ 356/237.5 |
| 6,155,699 | A | 12/2000 | Miller et al. |
| 6,163,036 | A | 12/2000 | Taninaka et al. |
| 6,200,134 | B1 | 3/2001 | Kovac et al. |
| 6,273,596 | B1 | 8/2001 | Parkyn, Jr. |
| 6,285,449 | B1 * | 9/2001 | Ellingson et al. .......... 356/237.1 |
| 6,291,839 | B1 | 9/2001 | Lester |
| 6,318,886 | B1 | 11/2001 | Stopa et al. |
| 6,319,425 | B1 | 11/2001 | Tasaki et al. |
| 6,328,456 | B1 | 12/2001 | Mize |
| 6,366,017 | B1 | 4/2002 | Antoniadis et al. |
| 6,367,950 | B1 | 4/2002 | Yamada et al. |
| 6,373,635 | B1 | 4/2002 | Fujimoto et al. |
| 6,375,340 | B1 | 4/2002 | Biebl et al. |
| 6,376,329 | B1 | 4/2002 | Sogard et al. |
| 6,419,384 | B1 | 7/2002 | Lewis et al. |
| 6,420,199 | B1 | 7/2002 | Coman et al. |
| 6,441,873 | B2 | 8/2002 | Young |
| 6,459,919 | B1 | 10/2002 | Lys et al. |
| 6,498,355 | B1 | 12/2002 | Harrah et al. |
| 6,525,335 | B1 | 2/2003 | Krames et al. |
| 6,534,791 | B1 | 3/2003 | Hayashi et al. |
| 6,536,923 | B1 | 3/2003 | Merz |
| 6,547,249 | B2 | 4/2003 | Collins, III et al. |
| 6,554,451 | B1 | 4/2003 | Keuper |
| 6,561,640 | B1 | 5/2003 | Young |
| 6,561,808 | B2 | 5/2003 | Neuberger |
| 6,573,536 | B1 | 6/2003 | Dry |
| 6,577,332 | B2 | 6/2003 | Osawa et al. |
| 6,578,986 | B2 | 6/2003 | Swaris et al. |
| 6,578,989 | B2 | 6/2003 | Osumi et al. |
| 6,607,286 | B2 | 8/2003 | West et al. |
| 6,630,689 | B2 | 10/2003 | Bhat et al. |
| 6,642,066 | B1 * | 11/2003 | Halliyal et al. ............... 356/369 |
| 6,683,421 | B1 | 1/2004 | Kennedy et al. |
| 6,686,581 | B2 | 2/2004 | Verhoeckx et al. |
| 6,704,089 | B2 * | 3/2004 | van der Schaar et al. ..... 356/400 |
| 6,708,501 | B1 | 3/2004 | Ghoshal et al. |
| 6,724,473 | B2 * | 4/2004 | Leong et al. ................ 356/237.4 |
| 6,734,960 | B1 * | 5/2004 | Goto et al. .................. 356/237.1 |
| 6,744,521 | B1 * | 6/2004 | Hertling et al. ................ 356/503 |
| 6,796,502 | B2 | 9/2004 | Nogami et al. |
| 6,796,698 | B2 | 9/2004 | Sommers et al. |
| 6,800,500 | B2 | 10/2004 | Coman et al. |
| 6,801,315 | B2 * | 10/2004 | Finarov et al. ................ 356/401 |
| 6,815,724 | B2 | 11/2004 | Dry |
| 6,822,991 | B2 | 11/2004 | Collins, III et al. |
| 6,831,303 | B2 | 12/2004 | Dry |
| 6,850,637 | B1 | 2/2005 | Burnett |
| 6,857,767 | B2 | 2/2005 | Matsui et al. |
| 6,930,870 | B2 | 8/2005 | Nobe et al. |
| 6,937,754 | B1 | 8/2005 | Eguchi |
| 6,992,335 | B2 | 1/2006 | Ohkawa |
| 6,995,348 | B2 | 2/2006 | Bradley et al. |
| 7,009,165 | B2 | 3/2006 | Hehemann et al. |
| 7,068,363 | B2 * | 6/2006 | Bevis et al. ................. 356/237.5 |
| 7,071,493 | B2 | 7/2006 | Owen et al. |
| 7,099,005 | B1 * | 8/2006 | Fabrikant et al. ............. 356/369 |
| 7,102,172 | B2 | 9/2006 | Lynch et al. |
| 7,116,481 | B2 * | 10/2006 | Syms ............................. 359/578 |
| 7,179,670 | B2 | 2/2007 | Shelton et al. |
| 7,271,921 | B2 * | 9/2007 | Shortt ........................... 356/630 |
| 7,554,656 | B2 * | 6/2009 | Shortt et al. ................ 356/237.5 |
| 2001/0002120 | A1 | 5/2001 | Bessendorf et al. |
| 2001/0007498 | A1 | 7/2001 | Arai et al. |
| 2001/0030782 | A1 | 10/2001 | Trezza |
| 2001/0046652 | A1 | 11/2001 | Ostler et al. |
| 2002/0053589 | A1 | 5/2002 | Owen et al. |
| 2002/0187454 | A1 | 12/2002 | Melikechi et al. |
| 2003/0038943 | A1 | 2/2003 | Almarzouk et al. |
| 2003/0175488 | A1 * | 9/2003 | Asthana et al. ................ 428/212 |
| 2003/0230765 | A1 | 12/2003 | Dry |
| 2004/0000677 | A1 | 1/2004 | Dry |
| 2004/0011457 | A1 | 1/2004 | Kobayashi et al. |
| 2004/0026721 | A1 | 2/2004 | Dry |
| 2004/0041521 | A1 | 3/2004 | Mandler et al. |
| 2004/0057873 | A1 | 3/2004 | Yerazunis et al. |
| 2004/0090794 | A1 | 5/2004 | Ollett et al. |
| 2004/0113549 | A1 | 6/2004 | Roberts et al. |
| 2004/0119084 | A1 | 6/2004 | Hsieh et al. |
| 2004/0134603 | A1 | 7/2004 | Kobayashi et al. |
| 2004/0135159 | A1 | 7/2004 | Siegel |
| 2004/0141326 | A1 | 7/2004 | Dry |
| 2004/0166249 | A1 | 8/2004 | Siegel |
| 2004/0206970 | A1 | 10/2004 | Martin |
| 2004/0207836 | A1 * | 10/2004 | Chhibber et al. ........... 356/237.4 |
| 2004/0238111 | A1 | 12/2004 | Siegel |
| 2005/0018179 | A1 | 1/2005 | Bevis et al. |
| 2005/0082480 | A1 | 4/2005 | Wagner et al. |
| 2005/0088380 | A1 | 4/2005 | Bulovic et al. |
| 2005/0098299 | A1 | 5/2005 | Goodson et al. |
| 2005/0152146 | A1 | 7/2005 | Owen et al. |
| 2005/0218468 | A1 | 10/2005 | Owen |
| 2005/0230600 | A1 | 10/2005 | Olson et al. |
| 2005/0253252 | A1 | 11/2005 | Owen et al. |
| 2005/0285129 | A1 | 12/2005 | Jackson, III et al. |
| 2006/0216865 | A1 | 9/2006 | Owen et al. |

FOREIGN PATENT DOCUMENTS

| | | |
|---|---|---|
| EP | 0935145 | 8/1999 |
| EP | 1158761 | 11/2001 |
| EP | 1469529 A2 | 10/2004 |
| GB | 2224374 | 5/1990 |
| GB | 2396331 A1 | 6/2004 |
| GB | 2399162 A | 9/2004 |
| JP | 404204333 | 7/1992 |
| JP | 2003268042 A | 9/2003 |
| WO | 9716679 | 5/1997 |
| WO | WO9854227 | 12/1998 |
| WO | 0037904 | 6/2000 |
| WO | 0102846 | 1/2001 |
| WO | 0206723 | 1/2002 |
| WO | 0213231 | 2/2002 |
| WO | 0226270 | 4/2002 |
| WO | WO03096387 A2 | 11/2003 |
| WO | WO2004009318 A1 | 1/2004 |
| WO | WO2004011848 A2 | 2/2004 |
| WO | WO2004038759 A2 | 5/2004 |
| WO | WO2004078477 A1 | 9/2004 |
| WO | WO2005041632 A2 | 5/2005 |
| WO | WO2005043598 A2 | 5/2005 |
| WO | WO2005043954 A2 | 5/2005 |
| WO | WO2005091392 A2 | 9/2005 |
| WO | WO2005094390 A2 | 10/2005 |
| WO | WO2005100961 A2 | 10/2005 |
| WO | WO2005101535 A2 | 10/2005 |
| WO | WO2006072071 A2 | 7/2006 |

OTHER PUBLICATIONS

PCT International Search Report and International Preliminary Examination Report dated Nov. 19, 2003 for International PCT Application No. PCT/US03/14625, filed May 8, 2003, 6 pages.

PCT International Search Report and Written Opinion dated Jun. 3, 2005 for International PCT Application No. PCT/US04/36260, filed Oct. 28, 2004, 5 pages.

PCT International Search Report and Written Opinion dated Jun. 17, 2005 for International PCT Application No. PCT/US04/36370, filed Nov. 1, 2004, 6 pages.

PCT International Search Report and Written Opinion dated Aug. 26, 2005 for International PCT Application No. PCT/US05/09407, filed Mar. 18, 2005, 11 pages.

PCT Preliminary Report on Patentability dated Oct. 13, 2006 for International PCT Application No. PCT/US05/13448, filed Apr. 19, 2005, 6 pages.

Related U.S. Appl. No. 10/984,589, filed Nov. 8, 2004—Electromagnetic Spectrum, 1 page, printed Aug. 16, 2006 www.brocku.ca/earthsciences/people/gfinn/optical/spectrum.gif.

Not yet published related U.S. Appl. No. 11/434,544, filed May 12, 2006 Specification and Figures; 28 pages.

Not yet published related U.S. Appl. No. 11/614,753, filed Dec. 21, 2006; Specification and Figures; 58 pages.

PCT International Search Report and PCT Written Opinion dated Oct. 13, 2006 for International PCT Application No. PCT/US05/13448, filed Apr. 19, 2005, 7 pages.

PCT International Search Report and PCT Written Opinion dated Sep. 28, 2006 for International PCT Application No. PCT/US05/11216 filed Mar. 30, 2005, 8 pages.

PCT International Search Report and PCT Written Opinion dated Oct. 16, 2006 for International PCT Application No. PCT/US05/09076 filed Mar. 18, 2005, 9 pages.

Not yet published related U.S. Appl. No. 11/342,363, filed Jan. 26, 2006; Specification and Figures; 44 pages.

Taiwan Intellectual Property Office, translation of Examination Report for corresponding Taiwan Patent Application No. 094112503, including Search Report, 4 pages, Mar. 11, 2007.

Stern, S. Alan and Cheng, Andrew; Edited by Nichols II, Ted A. "The New Horizons Spacecraft"; www.plutoportal.net/plutospacecraft.htm, The Pluto Portal, 3 pages, Aug. 16, 2007.

Supplemental European Search Report and written opinion for corresponding EU application No. EP03724539, dated Nov. 21, 2007, 8 pages total.

PCT International Search Report and Written Opinion dated Feb. 6, 2007 for International PCT application No. PCT/US2005/12608, filed Apr. 12, 2005, 9 pages.

PCT International Search Report and Written Opinion dated Feb. 27, 2008 for International PCT application No. PCT/US2005/47605, filed Dec. 30, 2005, 11 pages.

* cited by examiner

US 8,077,305 B2

IMAGING SEMICONDUCTOR STRUCTURES USING SOLID STATE ILLUMINATION

RELATED APPLICATIONS

This invention claims the benefit of co-pending U.S. Provisional Application No. 60/563,856, entitled METHOD AND APPARATUS FOR THROUGH-SUBSTRATE IMAGING AND INSPECTION OF BONDED SILICON WAFERS USING SOLID STATE ILLUMINATION, filed on Apr. 19, 2004, the entire disclosure of which is hereby incorporated by reference, as if set forth herein, for all purposes.

BACKGROUND OF THE INVENTION

The semiconductor industry is continually innovating in fabrication processes. This innovation has resulted, and will likely continue to result, in the development of new structures and, as such, new semiconductor devices. More specifically, this innovation has taken semiconductor fabrication from (a) having active circuitry in largely flat layers disposed substantially at or in the very top of a single semiconductor substrate, toward (b) providing active circuitry at one or more layers of various layers, in new substrates, or in combination(s) of substrates, including between two or more bonded or stacked substrates. This innovation has resulted in semiconductor devices such as Micro Electro Mechanical Systems (MEMS), Micro Electro Optical Mechanical Systems (MOEMS), Silicon on Insulator (SOI) devices and Light Emitting Diodes (LEDs).

Fabrication innovations in the semiconductor industry generally are accompanied by innovations in test and quality control. In test and quality control, tools and processes are employed that identify defects in particular chips/wafers, while also generally contributing to improvements in fabrication (e.g., process control so as to increase yield) and reliability (e.g., to anticipate and help control failure parameters of products in the field). Such tools and processes are directed, among other things, to imaging and inspecting semiconductor devices, particularly as to the semiconductor structures thereof. Accordingly, when fabrication innovation results in new semiconductor structures, innovations generally keep pace in tools and processes so as to enable imaging and inspection of such structures.

As would be expected for conventional semiconductor devices having active circuitry substantially at or near the surface of a single semiconductor substrate, conventional imaging and inspection tools and processes are employed. These tools and processes enable identification of features located substantially at or near the wafer's surface, e.g., within approximately 200 Angstroms of the wafer's surface. Clearly, these tools and processes have capabilities paired to the structures that are to be imaged or inspected.

As for conventional semiconductor devices, new semiconductor devices generally need tools and processes that enable imaging and inspection of device's structure(s)'s relevant features, including to identify various conditions and to detect defects. However, these relevant features may be disposed other than at or near the surface of the substrate. Indeed, these relevant features within bonded or stacked substrates tend to be located inside the bonded or stacked layers (e.g., in the interface layer(s), including the characteristics of the bond itself). As such, for these and other new semiconductor devices, conventional imaging and inspection tends generally to be insufficiently effective, or even ineffective, if performed using the above-described conventional tools and processes.

Tools and processes have been developed that enable imaging and inspection of features relevant to the structure(s) of the above described semiconductor devices. To illustrate, tools and processes exist for imaging and inspection of semiconductor devices having bonded or stacked substrates, or other structures based on bonding or stacking materials. These tools and processes include infrared microscopy using high magnification optics under infrared light provided by bulbs; X-Ray imaging; and ultrasonic imaging.

Of these, ultrasonic imaging may be the most prevalent. It entails placing a wafer in a liquid bath, applying an ultrasonic signal and, using ultrasound wave flight measurement, constructing a map of the wafer bond's integrity. Even though prevalent, ultrasonic imaging has several drawbacks. These drawbacks include, as examples: the liquid bath tends to be detrimental to electronic production environments; it not only adds the steps described above, but also introduces additional steps before fabrication can proceed (e.g., to clean and dry the wafer); and it enables only the inspection for wafer bond defects, such that other relevant conditions or defects are identified/detected using additional imaging/inspection tools and/or processes.

The drawbacks of ultrasonic imaging are not present in infrared microscopy. Infrared microscopy, as illustrated in FIG. 1, typically entails using a halogen or other bulb light source 10 in conjunction with an appropriate infrared high-pass or band-pass filter 20 so as to generate infrared light. The infrared light is provided to irradiate objects 50 via a fiber optic light guide 2 and a lens system 3. In this configuration, the infrared light is directed to objects 50 via an internal beam splitter in the lens system 3. The infrared light, so directed, generally is reflected by objects 50 at various intensities (e.g., depending on the bond characteristics and other structural features of the semiconductor device) back up through the lens system 3 to an infrared camera 60 for image capture. Via such image, test and quality control may be performed, e.g., to inspect the relevant features, including to identify various conditions and to detect defects, such as in bonding and adjacent layer(s).

While infrared microscopy provides for imaging and inspection of semiconductor devices having bonded or stacked substrates, microscopy also tends to have drawbacks. As an example, a typical light source is a halogen or other bulb, which provides light across a broad spectrum, including infrared. In order to provide infrared light, then, an appropriate filter is used. As another example, a typical infrared camera in conventional microscopy arrangements is or employs, e.g., a vidicon camera, gallium arsenide detectors, microbolometers, or other scientific, professional or industrial-grade technologies which technologies tend to be technically more complex to develop, manufacture and use, while also tending to be produced in lower volumes and at higher costs than mainstream solid state imaging devices (e.g., standard, consumer-grade, silicon-based charge coupled devices or CMOS image sensors, used in, for example, consumer digital still cameras that are widely sold to average consumers in retail outlets).

Accordingly, it is desirable to have tools and processes that broadly enable imaging and inspection of the various features relevant to selected structure(s) of semiconductor devices. In addition, it is desirable to have tools and processes that enable imaging and inspection of features relevant to selected structure(s) of semiconductor devices, particularly where such structures and associated features are disposed other than at or near the surface of the device.

SUMMARY OF THE INVENTION

The present invention provides tools and processes that broadly enable imaging and inspection of the various features relevant to selected structure(s) of semiconductor devices.

The present inventions also provides tools and processes that enable imaging and inspection of features relevant to selected structure(s) of semiconductor devices, particularly where such structures and associated features are disposed other than at or near the surface of the device. The present invention also provides tools and processes that enable imaging and inspection of features relevant to selected structure(s) of semiconductor devices, where such relevant features (such as defects) are associated with bonded or stacked layers (e.g., in the interfacing layer(s) of bonded or stacked substrates or in the bond itself) or with other bonded or stacked materials.

The present invention also provides tools and processes that have enhanced source(s) of radiation, particularly infrared radiation. Such source(s) are variously enhanced, including, as examples, as to selectivity of the radiation's wavelength(s) (including variations therein, e.g., over time), control and quality of collimation (as well as selected departures therefrom, including as a function of wavelength), control and quality of coherence (as well as selected departures therefrom), control over intensity (e.g., selected variations therein, including as a function of wavelength), control over duty cycle (e.g., from pulsed to continuous, including as a function of wavelength), as well as other characteristics of the source and/or its radiation.

The present invention also provides tools and processes that employ infrared camera(s) based on or using either or both scientific-grade and/or mainstream solid state imaging devices.

The present invention also provides tools and processes that—as to infrared wavelength(s) capable of imaging selected, relevant features of a selected semiconductor structure—couple a light source and a solid state imaging device, such that the light source is enabled to provide such infrared wavelength(s) and the imaging device is appropriately responsive to such wavelength(s). In this example embodiment, the infrared wavelength(s) may be selected not only for ability to detect such features, but also for transmissiveness through the entire semiconductor structure. Moreover, in this example embodiment, the imaging device preferably also has sufficient resolution to properly image the condition or defect being imaged. In this embodiment, the light source preferably is enabled to provide such infrared wavelength(s), e.g., (a) to the exclusion of other wavelengths, at least at some selected time and/or for a selected time duration) and (b) with selected characteristics, including as to intensity, collimation, and the like.

The present invention also provides tools and processes that—as to radiated wavelength(s) capable of imaging selected, relevant features of a selected semiconductor structure—couple a light source and a solid state imaging device (e.g., camera based on such device), such that the light source is enabled to provide such wavelength(s) and the imaging device is appropriately responsive to such wavelength(s). In this example embodiment, certain wavelength(s) may be selected not only for ability to detect such features, but also for transmissiveness through the entire semiconductor structure, e.g., infrared wavelengths. Moreover, so as to enable or enhance imaging and inspection, the selected wavelengths may include combinations of wavelengths or bands of wavelengths among one or more of the visible, infrared and/or ultraviolet spectra, simultaneously or at different times. In this example embodiment, the imaging device preferably also has sufficient resolution to properly image the condition or defect being imaged. This example embodiment also contemplates one or more imaging devices, wherein each imaging device may be tuned to specific wavelength(s) or band(s) of wavelengths based, e.g., on the respective device's sensitivity to such wavelengths and/or its ability to resolve features sought to be imaged. In this embodiment, the light source preferably is enabled to provide such infrared wavelength(s), e.g., (a) to the exclusion of other wavelengths, at least at some selected time and/or for a selected time duration) and (b) with selected characteristics, including as to intensity, collimation, and the like.

In a general embodiment in accordance with this invention, tools and processes are provided which recognize and respond to the quantum efficiencies and other physical properties of solid state imaging devices. Such tools and processes preferably respond to and result from coordination of various facts and factors, including: (a) the particular, to-be-imaged semiconductor structure has known or determined semiconductor materials (and associated band-gap energy or energies) and may have features of known or determined parameters, including as to typical size, shape and location; (b) radiation wavelength(s) or band(s) of wavelength(s) are selected based on such materials, energies, and parameters, as well as the orientation of the radiation source and subject to the spectral response of the imaging device; (c) the radiation source is selected and oriented, which radiation source is enabled both to provide the selected wavelengths, to control radiation characteristics (including as to intensity, collimation, lack of collimation, pulsing, etc.), and to deliver the radiation at appropriate orientations (e.g., angles and locations, including from the back side of the structure) relative to the semiconductor structure; (d) a lens system is selected so as to transmit the selected wavelengths to the imaging device and to match the lens' image-forming capabilities with the imaging device's image-capture capabilities (e.g., the lens is able to resolve features of size equal to, or less than, the feature sizes that the imaging device resolves), so as to properly image the features; and (e) the imaging device is able to capture an image of the features, based on sufficient sensitivity to the selected wavelength(s) and having sensor cell size and number sufficient to resolve the imaged features, as well as proper delivery of the selected radiation. To illustrate, when imaging based on a radiation orientation that directs the selected wavelength(s) to the back side of the structure, the radiation source preferably provides infrared wavelength(s) that may be transmitted entirely through the to-be-imaged structure and that are half or less than half the relevant dimensions of the feature to be detected. Moreover, the radiation source preferably (i) provides the selected wavelengths (e.g., at appropriate intensities and for sufficient durations) so as to enable the imaging device to capture the image based on the selected wavelengths, i.e., despite the device's relative insensitivity to such wavelengths, while (ii) excluding all other wavelengths so that the imaging device's sensor cells are not electrically saturated by such other wavelengths.

These and other embodiments are described in more detail in the following detailed descriptions and the figures.

The foregoing is not intended to be exhaustive of all embodiments and features of the present invention. Persons skilled in the art are capable of appreciating other embodiments and features from the following detailed description in conjunction with the drawings.

DETAILED DESCRIPTION OF THE INVENTION

Figure 1:
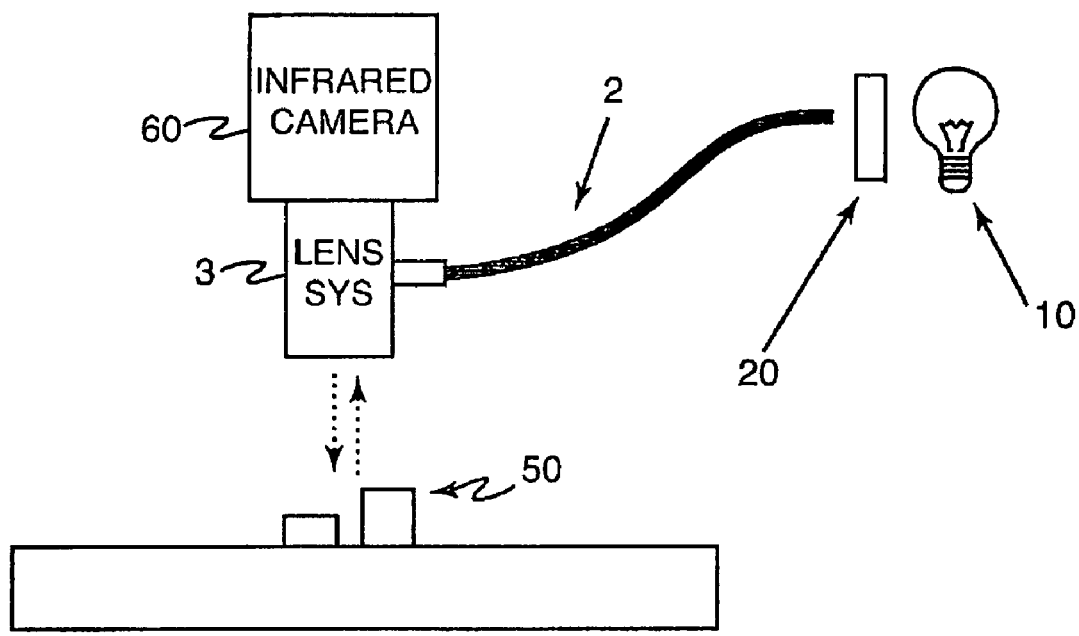
FIG. 1 is a schematic diagram of a conventional infrared microscopy arrangement using an IR bulb and filter.

Representative embodiments of the present invention are shown in FIGS. 1-19, wherein similar features share common reference numerals.

Solid State Imaging Devices

Solid state imaging devices (e.g., charge coupled devices (CCDs) or CMOS image sensors) have been developed that (a) sense incident radiation and (b) where such incident radiation is representative of an image, capture such image. These imaging devices respond to, and perform based on, the known physical relationship among semiconductors and incident radiation which relationship, generally, provides that photons may interact with silicon to produce electric charge. Though known, the relationship is a relatively complex function involving various factors, including the incident light's wavelength, the implicated semiconductor material(s), and the semiconductor material's doping (e.g., the dopant (s), concentration(s) and dimensional profiles of such doping). This relationship provides, for selected wavelengths in the infrared spectrum, that semiconductor materials tend to be more or less transmissive of incident radiation.

In this relationship, the implicated semiconductor material's band-gap energy figures prominently. This band-gap energy is a constant. Generally, this band-gap energy represents the minimum amount of energy required for an electron to jump an energy band (e.g., from a valence band to the conduction band). This band-gap energy, for the particular semiconductor material, follows the formula:

$$E_e(\text{material}) = hc/\lambda$$

$$E_e(\text{material}) = \eta c/\lambda$$

where h is Plank's constant, c is the velocity of light in vacuum and $\lambda$ is the wavelength of incident radiation.

Applied to imaging, the above formula may be restated to describe each semiconductor material's critical wavelength for incident radiation, as follows:

$$\lambda_c > hc/E_e(\text{material})$$

This restated formula may be used to determine whether or not, in the collision of a photon of a specific wavelength with an atom of a particular semiconductor material, any electrons are likely to be excited from the valence band to the conduction band due to the reaction between the photons and orbital electrons. Above the material-specific critical wavelength $\lambda_c$, the incident radiation's photons are unlikely to so excite an electron and, as such, the photons are unlikely to produce charge for image capture. Conversely, when a particular semiconductor material is subject to incident radiation of a wavelength at or below $\lambda_c$ (i.e., corresponding to energy above the material's band-gap energy), the collision of photons with the material's atoms is likely to excite valence-band electron(s) into the conduction band.

When incident radiation exceeds a material's critical wavelength $\lambda_c$, the radiation's photons tend to penetrate either deeply into or completely through the material. Table 1 below lists the band-gap energy and critical wavelength (calculated using such energies) for each of a variety of materials. From this table, it is apparent that typical substrate materials such as germanium, silicon and gallium arsenide are characterized by critical wavelengths in the infrared spectrum, particularly the near infrared spectrum.

TABLE 1

| Material | Band-gap Energy (eV) | Critical Wavelength (µm) |
|---|---|---|
| Ge | 0.67 | 1.85 |
| Si | 1.1 | 1.127 |
| GaAs | 1.4 | 0.886 |
| CdSe, n | 1.7 | 0.729 |
| GaP | 2.25 | 0.551 |
| CdS, n | 2.4 | 0.517 |
| ZnS, n | 3.5 | 0.354 |

Table 2 below is representative of the depth to which incident photons tend to penetrate a model, silicon-based CCD. From this table, it is apparent that penetration (and conversely, absorption) of photons in silicon, as well other semiconductor materials, is wavelength dependent. Indeed, as incident radiation goes further into the infrared spectrum, photons tend to penetrate ever more deeply into the semiconductor material. That is, in a solid state imaging device, photons of ever longer infrared wavelengths tend to penetrate more deeply into the bulk of the substrate. Where penetration exceeds the thickness of the device's substrate, the incident radiation may pass through the substrate, and device, entirely. It is noted, however, that the penetration depth (and, conversely, absorption) of a photon into a silicon-based CCD, or other solid state imaging device, will tend also to depend on other structures (e.g., passivation layers, oxide layers, metal and polysilicon interconnect layers, diffusion layers, active layer shielding elements, protective windows etc.) which the photon may encounter along the way.

TABLE 2

| Wavelength (Nanometers) | Penetration Depth (Microns) |
| --- | --- |
| 400 | 0.19 |
| 450 | 1.0 |
| 500 | 2.3 |
| 550 | 3.3 |
| 600 | 5.0 |
| 650 | 7.6 |
| 700 | 8.5 |
| 750 | 16 |
| 800 | 23 |
| 850 | 46 |
| 900 | 62 |
| 950 | 150 |
| 1000 | 470 |
| 1050 | 1500 |
| 1100 | 7600 |

When a photon is absorbed by a solid state imaging device, as previously described, electronic charge is generated through the excitation of valence-band electron(s) into the conduction band (i.e., creating an electron and a hole). The amount of electronic charge generated in connection with the photon depends on various factors. These factors include the radiant power density of the radiation incident on the device, the total duration of irradiation of the device and, if pulsed, the duty cycle of the radiation. Generally, greater power density results in greater charge generation. Similarly, greater irradiation duration and duty cycle (e.g., approaching or being continuous irradiation) also result in greater charge generation.

Charge generation factors also include: the diffusion length and recombination rate of the liberated electron (or hole); the chemical and physical nature of materials overlying the device's surface (e.g., shielding elements); and the location and depth at which the photon is absorbed (relative to the location and depth of relevant circuit structures). As to the lattermost factor, if photons are absorbed at locations and depths in the potential well of, e.g., a CCD, the photons are likely to generate charge that will be effective in the CCD's imaging operations. Conversely, if photons are absorbed deep in the CCD's substrate, any electron-hole pairs created by the photons may be more likely to recombine before contributing to the device's imaging operation. In that case, the photons are ineffective in the CCD's imaging operations.

Figure 2:
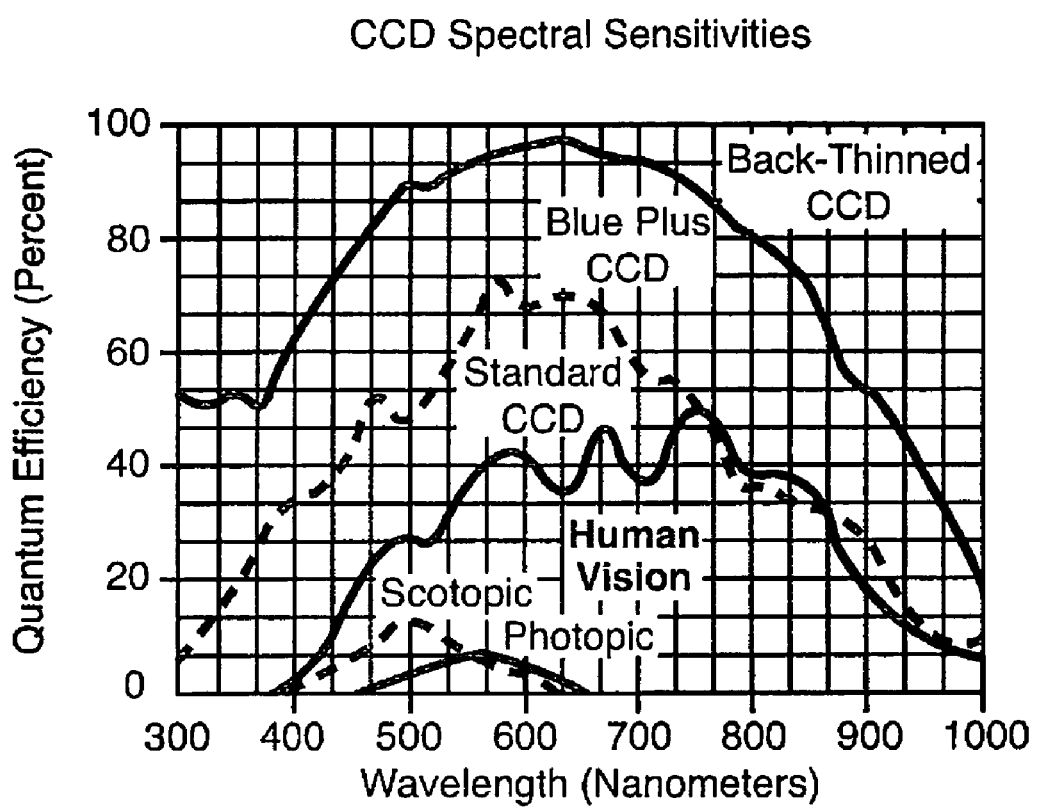
FIG. 2 shows representative quantum efficiency curves of several model CCDs, as well as of a typical human eye.

In solid state imaging devices, like CCDs and CMOS sensors, a device's responsiveness in converting incident radiation to charge effective for the device's imaging operations typically is known as "quantum efficiency". FIG. 2 shows representative quantum efficiency curves of several model CCDs (i.e., these CCDs and the curves do not necessarily correspond to any actual devices or curves, but are meant to typical of the devices and curves). FIG. 2 also shows correlative responsiveness of the typical human eye. In doing so, FIG. 2 provides data extending from the longer wavelengths of the ultraviolet light spectrum, across the visible light spectrum and into the near infrared light spectrum. As is apparent from FIG. 2, the human eye's photopic and scotopic vision (i.e., arising from cones and rods, respectively) is far less sensitive than typical CCDs, both as to any individual wavelength and in terms of the range of wavelengths. As is also apparent from FIG. 2, the model CCDs tend to have more substantial quantum efficiency (and, thus, sensitivity) in the visible light spectrum, with diminishing response at and into the near infrared spectrum. These conclusions are expected to apply similarly to typical CMOS sensors as well as solid state imaging devices generally.

FIG. 2 also illustrates that among solid state imaging devices, including these model CCDs, some will exhibit quantum efficiencies that are superior to others. FIG. 2 illustrates this using representative quantum efficiency curves for model CCDs that are labeled, respectively, as standard, "back thinned" and "blue plus". Compared to the standard CCD, the "back thinned" and "blue plus" CCDs generally exhibit enhanced performance across most of the spectrum (subject to (a) ripples thought to be due to antireflective films often used on protective windows found in many CCDs and (b) slight performance degradation of the "blue plus" in approximately 750-875 nm range).

Certain enhanced-performance CCDs, such as those illustrated in FIG. 2, characterize a device category often referred to in the industry as "scientific-grade" (also sometimes referred to as "professional-grade" or other such terms). Generally, scientific-grade solid-state imaging devices offer various advantages over mainstream solid state imaging devices (e.g., the standard consumer-grade, silicon-based, imaging devices used in, for example, digital still cameras widely sold to average consumers in retail outlets). As illustrated already, one typical advantage is enhanced quantum efficiencies, typically either across a broad spectrum as in FIG. 2 or as to a specific section of interest. Other advantages typically include, as examples: higher signal to noise ratios, larger dynamic ranges, fewer defects, lower noise, enhanced gain uniformity across the array of sensors, and enhanced control of the chip's operations (e.g., control over read-out rates and shutter speeds, as well as over performance enhancement features, such as "binning" which pools the charge of a select number of adjacent sensor cells).

Figure 3:
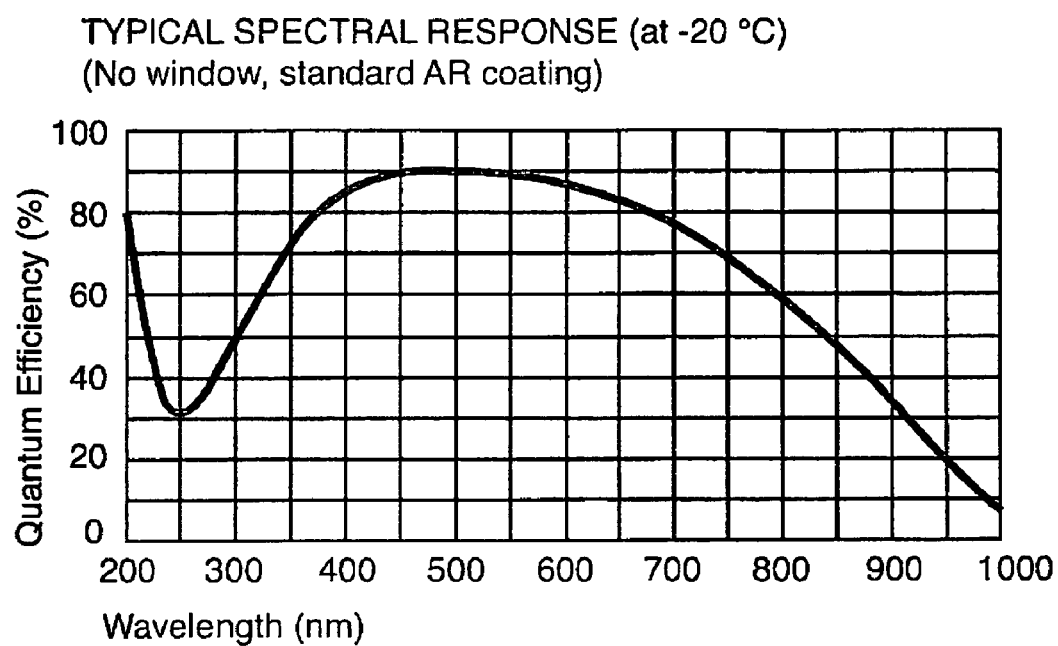
FIG. 3 shows the spectral response of a typical, high performance CCD.

However, scientific imaging devices also tend to have disadvantages. Typical disadvantages include, for example, that they tend to be technically more complex to develop, manufacture and use, while also tending to be produced in lower volumes and at higher costs than mainstream solid state imaging devices. As well, compared to mainstream solid state imaging devices, scientific-grade, solid state imaging devices generally have relatively large dimensions for each sensor cell, together with either relatively few pixels or relatively large total array size. To illustrate, scientific-grade devices typically have unit sensor cell sizes ranging from about 4.65 microns to as much 24 microns on a side, with typical sizes tending to be between 6.5 and 9 micron. These devices have pixel numbers ranging from the low thousands up to approximately 8 megapixels, but with typical pixel numbers tending to be between 0.3 and 1.5 megapixels. These devices have various total array areas; however, for those example devices having 3-6 megapixels, the total array area tends to exceed 20 mm (measured on the diagonal). An example is the Marconi Applied Technologies CCD39-01 sensor, which is a back illuminated CCD having square unit sensor cells, each such cell having sides of 24 microns. This chip has a pixel number of 80×80 pixels (6400 pixels total), and a total array area of only 1.92 mm×1.92 mm. This chip's quantum efficiency curve is shown in FIG. 3. The curve exhibits little to no ripple, which is thought to follow from the absence of antireflective coating. As well, this curve's exhibits substantial quantum efficiency across a broad spectrum of wavelengths, from the ultraviolet into the infrared, which quality may reflect, in addition to other design and fabrication choices, either/both the absence of a protective window over the sensor cells and/or possibly the absence of an infrared cut-off filter (i.e., an optical filter blocking infrared wavelengths).

Another example of a scientific-grade CCD is the Sony ICX285AL. This chip provides 1.5 megapixels, wherein each unit sensor cell is 6.45 micron×6.45 micron. This chip has a total array area of 11 mm (on the diagonal). By comparison, mainstream solid state imaging devices having the same total array area of 11 mm as the Sony chip typically provide 6-8 megapixels, wherein each unit sensor cell is at or below 2.5 microns per side.

Scientific-grade imaging devices generally are specified and used as a matter of industry practice for cameras and systems directed to imaging and inspection of semiconductor structures. Generally, such specification is weighted based on the larger sensor cell sizes typical of scientific-grade imaging devices, i.e., relative to mainstream imaging. Larger sensor cell sizes enable collection of larger amounts of charge over a fixed exposure time or, similarly, enable collection of a required amount of charge over a shorter period of time. As well, larger sensor cells promote greater signal to noise ratios and greater dynamic range (i.e., so as enable clear recognition of both bright and dim areas in an image). As well, as previously described, quantum efficiencies may be important in any particular application, whether at a particular wavelength, across a range of wavelengths or in a particular band of interest.

In an example embodiment in accordance with this invention, one or more scientific-grade imaging devices are used for cameras and systems directed to imaging and inspection of semiconductor structures. To illustrate, one or more such scientific-grade imaging devices may be employed in tools and processes that enable imaging and inspection of features relevant to selected structure(s) of semiconductor devices, particularly where such structures and associated features are disposed other than at or near the surface of the device. To further illustrate, such imaging devices are employed to image and inspect relevant features (including various conditions and defects) associated with bonded or stacked layers (e.g., in the interfacing layer(s) of bonded or stacked substrates or in the bond itself) or with other bonded or stacked materials. To so image and inspect, the one or more imaging devices preferably are coupled with one or more radiation source(s), particularly enhanced source(s) of radiation. Where certain wavelength(s) are beneficial or otherwise required to image selected, relevant features of a selected semiconductor structure, the imaging device preferably is (a) coupled to one or more radiation sources that provide such wavelength(s) and (b) appropriately responsive to such wavelength(s). In providing such certain wavelength(s), the radiation source(s) may exclude other wavelengths, at least at some selected time and/or for a selected time duration. In this example, the certain wavelengths may include infrared wavelengths alone, or in combination with wavelengths of the visible or ultraviolet spectra, such combination being simultaneously or at different times. This example also contemplates one or more imaging devices, wherein each imaging device maybe tuned to specific wavelength(s) or band(s) of wavelengths.

In another example embodiment in accordance with this invention, one or more mainstream solid state imaging devices may be used. Generally, one or more mainstream imaging device may be substituted for selected or all imaging devices in the example embodiment described above relating to use of scientific-grade solid state imaging devices. Such use is either alone or in conjunction with one or more scientific-grade imaging devices.

In another example embodiment, mainstream devices may be used, e.g., to image and inspect features relevant to selected structure(s) of semiconductor devices, particularly where such features have sizes more compatible, in the context of the imaging system, to imaging with the typically smaller sensor cells of the mainstream imaging device, than with the sensor cells of the scientific-grade imaging device. Generally, such use of mainstream devices due to smaller sensor cells may introduce sensitivity, signal to noise and dynamic range issues, with attendant ramifications, e.g., in the provision of radiation and exclusion of noise. Moreover, to provide proper (e.g., sharp imaging), the lens system may lead to use of higher quality lens systems, at least higher quality than may typically be associated with scientific-grade imaging devices (e.g., due to the relatively larger sensor cells and array area).

In another example embodiment, mainstream devices may be used, e.g., to image and inspect such features where such features are capable of being imaged and inspected via certain wavelength(s) (e.g., infrared wavelengths), to which wavelengths the mainstream imaging device is appropriately responsive, while the scientific-grade device either is not responsive or not any more responsive. In either of these embodiments, the selected wavelength(s) may be such that the features may be imaged or inspected either best or only with such wavelength(s).

Figure 4:
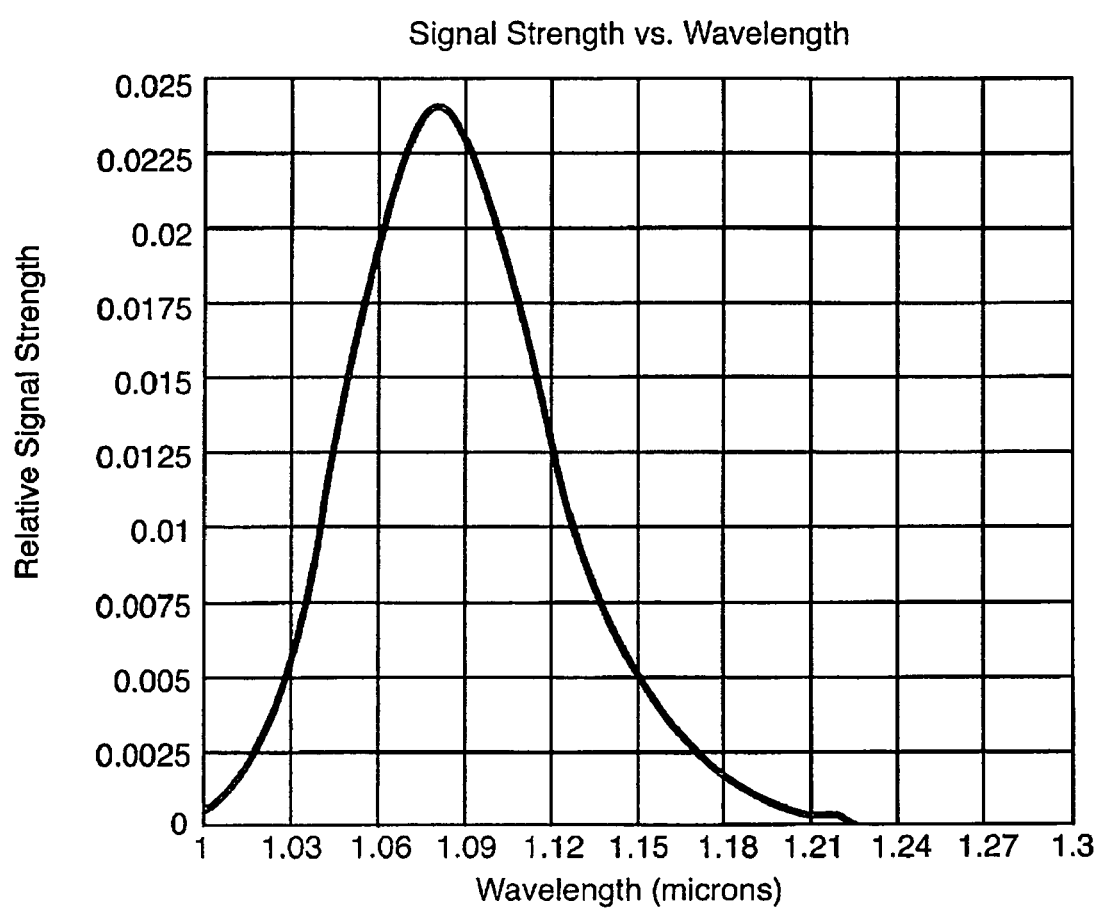
FIG. 4 shows an example of a representative composite sensitivity for a hypothetical imaging device.

Generally, in using solid state imaging devices, the imaging device should have sufficient sensitivity (or, equivalently for our purposes, have sufficient quantum efficiency) at the selected radiation wavelength(s) (e.g., such wavelengths being selected based on the expected defect's size and/or to enable imaging through the material or structure under consideration). However, as previously described, including with reference to FIG. 2, solid state imaging devices, including both scientific-grade and mainstream devices, generally exhibit diminishing sensitivity as the radiation wavelengths extend into the infrared spectrum. Accordingly, where the selected radiation wavelength(s) approach or are in the infrared spectrum, an example embodiment in accordance with the invention provides for modification of the imaging devices so as to obtain sufficient sensitivity. One such modification entails removal of a mainstream imaging device's infrared cut-off filter, which filters typically are found in mainstream solid state imaging devices (e.g., often affixed on top of, or otherwise above, the sensor array), but typically not found in scientific-grade imaging devices. Another modification entails altering the design and fabrication of the imaging device(s) so as to provide doping profiles (e.g., in or about each sensor cell's potential well) or other alterations, so as to increase the probability of absorption of photons in or around the selected (e.g., infrared) spectrum. The former modification tends to increase sensitivity generally through the previously blocked infrared wavelengths. The latter modification may be employed to improve sensitivity less broadly, e.g., as to more limited bands. These and other modifications preferably are employed to improve the imaging device's sensitivity to the selected wavelength(s).

Where the radiation wavelength(s) are selected so as to be transmitted entirely through the semiconductor materials being imaged and inspected, a composite wavelength sensitivity may be associated with an embodiment in accordance with the invention, which sensitivity generally is a function of both transmitted radiation (e.g., characterized by spectrum and optical power thereof) and the imaging device's spectral sensitivity. An example of a representative composite sensitivity is illustrated in FIG. 4. It is understood, as well, that when radiation wavelengths area selected for reflection by the semiconductor materials being imaged and inspected, a composite sensitivity may also be associated with an embodiment in accordance with the invention, which sensitivity similarly is a function of both the reflected radiation (e.g., characterized by spectrum and optical power thereof) and the imaging device's spectral sensitivity.

Lighting

Generally, embodiments in accordance with the invention provide tools and processes that preferably employ enhanced-performance source(s) of radiation, particularly radiation selected in coordination with the other components of the tools and processes contemplated in the invention. Such enhanced radiation source(s) may have various features and/or advantages over more conventional sources of the selected radiation (e.g., over bulbs). Examples of such features and/or advantages are directed to one or more of: selectivity of the radiation's wavelength(s) (including variations therein, e.g., over time); control over, and quality of, collimation (as well as selected departures therefrom, including as a function of wavelength); control and quality of coherence (as well as selected departures therefrom); quantity and control over intensity (e.g., providing variations of intensity, including as a function of wavelength); control over duty cycle (e.g., from pulsed to continuous, including as a function of wavelength), as well as other characteristics of the source and/or its radiation.

In an example embodiment in accordance with the invention, the radiation source provides radiation in one or more selected, narrow band(s). The source's radiation band typically may be characterized by its central wavelength, e.g., 1070 nm. The source preferably provides radiation using an array of one or more light emitting diodes (LEDs) and, in application, does so in connection with a selected orientation relative to the to-be-imaged structure (e.g., top lighting, side lighting, etc.). LED arrays having various enhanced features are shown and described in (a) U.S. patent application No. 11/084,466 filed Mar. 18, 2005, entitled "MICRO-REFLECTORS ON A SUBSTRATE FOR HIGH-DENSITY LED ARRAY", which application claims priority from U.S. Provisional Application Ser. No. 60/554,628, filed Mar. 18, 2004, (b) U.S. patent application No. 11/083,525 filed Mar. 18, 2005, entitled "DIRECT COOLING OF LEDS", which application claims priority from U.S. Provisional Application Ser. No. 60/554,632, filed Mar. 18, 2004, (c) U.S. patent application No. 11/095,210 filed Mar. 30, 2005, entitled "LED ARRAY HAVING ARRAY-BASED LED DETECTORS", which application claims priority from U.S. Provisional Application No. 60/558,205, filed Mar. 30, 2004, and (d) U.S. patent application Ser. No. 10/984,589, filed Nov. 8, 2004, entitled "HIGH EFFICIENCY SOLID-STATE LIGHT SOURCE AND METHODS OF USE AND MANUFACTURE"; the contents of all such applications of which are hereby incorporated by reference, as if recited in full herein, for all purposes.

Figure 5:
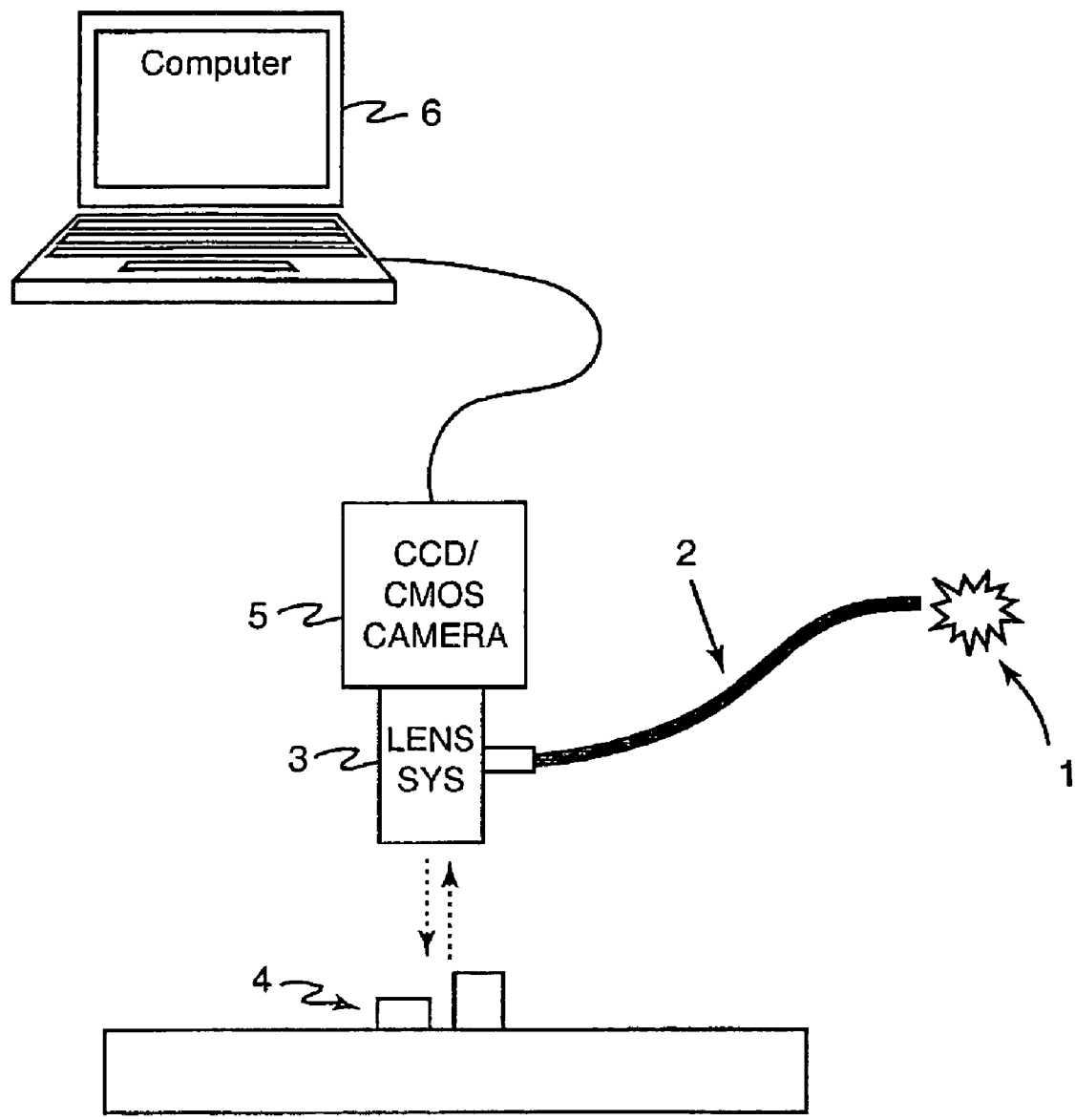
FIG. 5 shows a first example embodiment in accordance with the invention.

FIG. 5 shows a first example embodiment in accordance with the invention. There, a solid state light source 1 irradiates selected semiconductor structures 4 via a fiber optic light guide 2 and a lens system 3. The source's radiation is directed to structures 4 via an internal beam splitter in the lens system 3. The radiation, so directed, generally is reflected by structures 4 at various intensities (e.g., depending on the bond characteristics and other features and defects of the semiconductor structures), so as to travel back up through the lens system 3, to a camera 5, such camera being based on or using one or more solid state imaging devices, e.g., CCD or CMOS detectors. The camera 5 preferably detects such reflected radiation of one or more wavelengths. Via such detection, an image of the structures 4 is captured. The image, so captured, may be provided for further processing via, e.g., computer 6. The captured image, so processed or otherwise, may be employed for test and quality control, toward identifying relevant features of such structures 4, e.g., where such relevant features are associated with bonded or stacked layers (e.g., in the interfacing layer(s) of bonded or stacked substrates or in the bond itself) or with other bonded or stacked materials.

Figure 6:
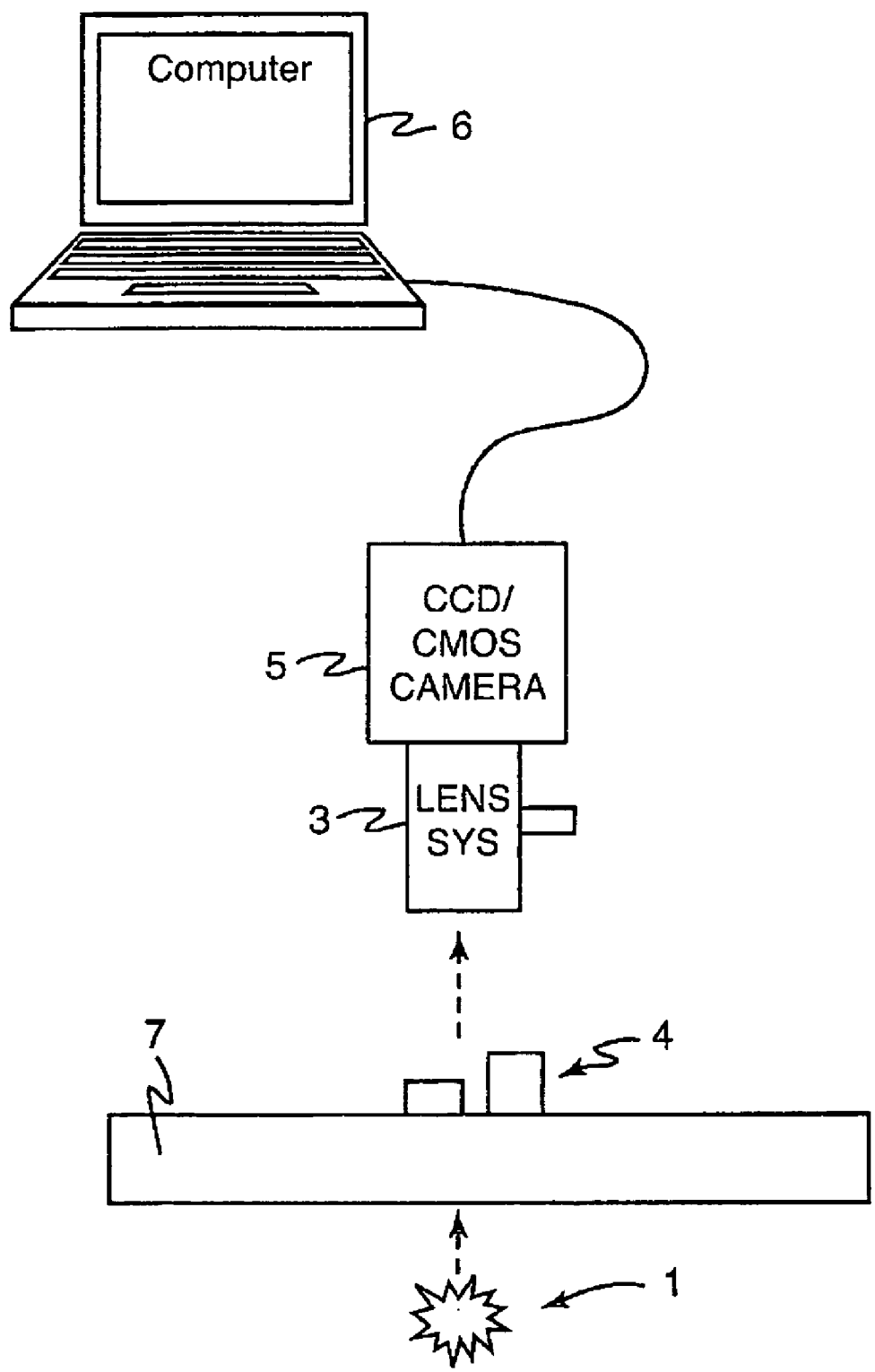
FIG. 6 shows a second example embodiment in accordance with the invention.

In a second example embodiment, shown in FIG. 6, the radiation source 1 is oriented on the side of the to-be-imaged structures 4 opposite the lens system 3 and camera 5, so as to provide back light. In this orientation, the source's radiation is transmitted through the structures 4 (as well as, through the substrate 7 of the semiconductor device having such structures 4) at different intensities to the lens system 3 for image formation on the CCD/CMOS camera 5. The image, so captured, may be provided for further processing via, e.g., computer 6. As with the first example embodiment, the captured image, so processed or otherwise, may be employed for test and quality control, toward identifying relevant features of such structures 4. In this back light orientation, transmission of the radiation through the structures 4 and substrate 7 will depend on various factors, as previously described, including the absence of metal or other interconnect layers or other materials which would block the transmission of the radiation, or reflect it away from the lens system 3.

Figure 7:
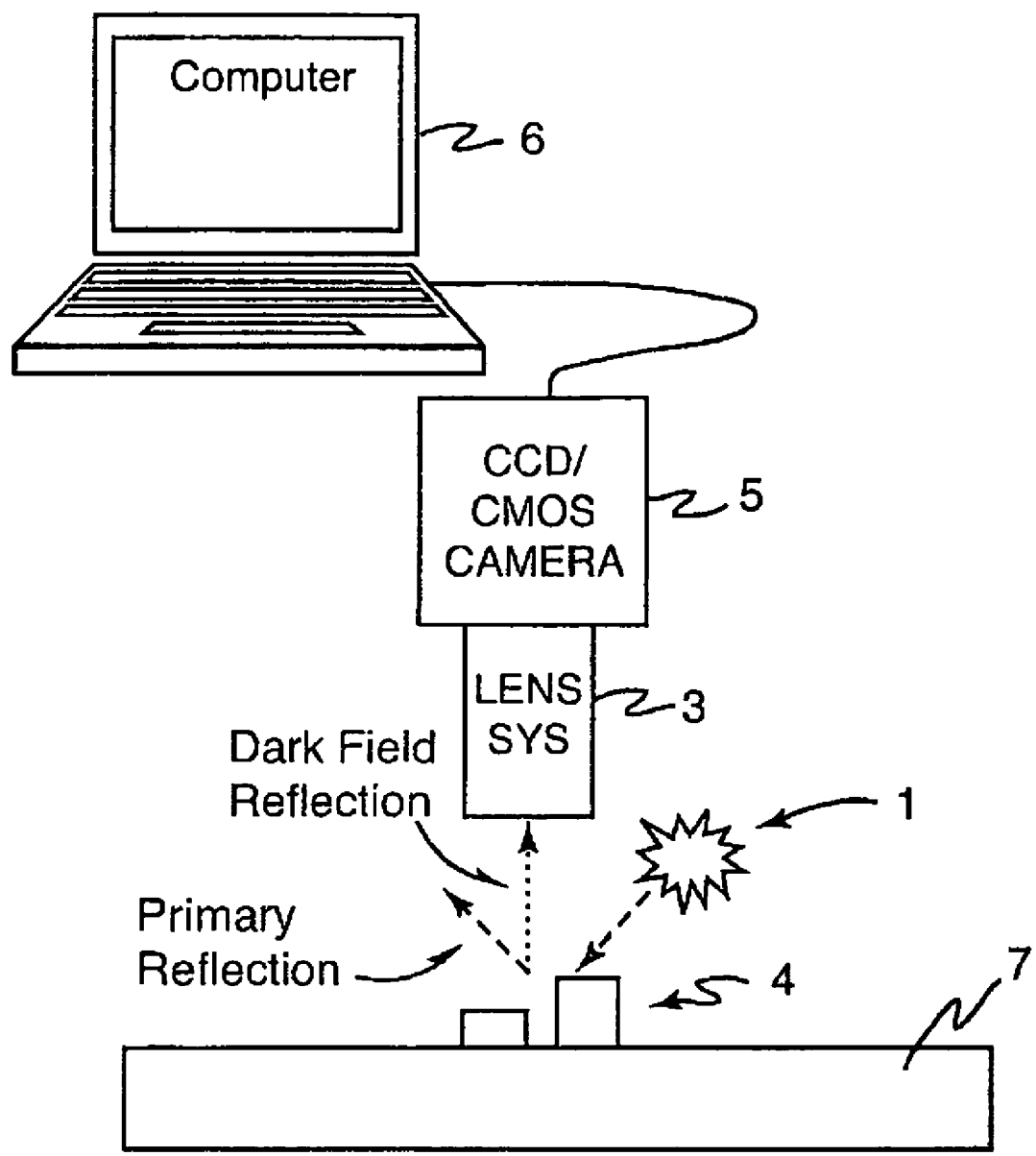
FIG. 7 shows an a third example embodiment in accordance with the invention.

In a third example embodiment, shown in FIG. 7, the radiation source 1 is oriented to the side of the to-be-imaged structures 4. Whereas most of the source's radiation will tend to be reflected by the substantially flat surface of the substrate 7 away from the lens system 3 so as to be unavailable for image capture via CCD/CMOS camera 5, the structures 4 will cause dark field reflections perpendicular to the substrate's surface. Since such reflections respond to the structures (e.g., topology, conditions and other features), such orientation is generally suitable for providing higher contrast imaging and inspection.

Figure 8:
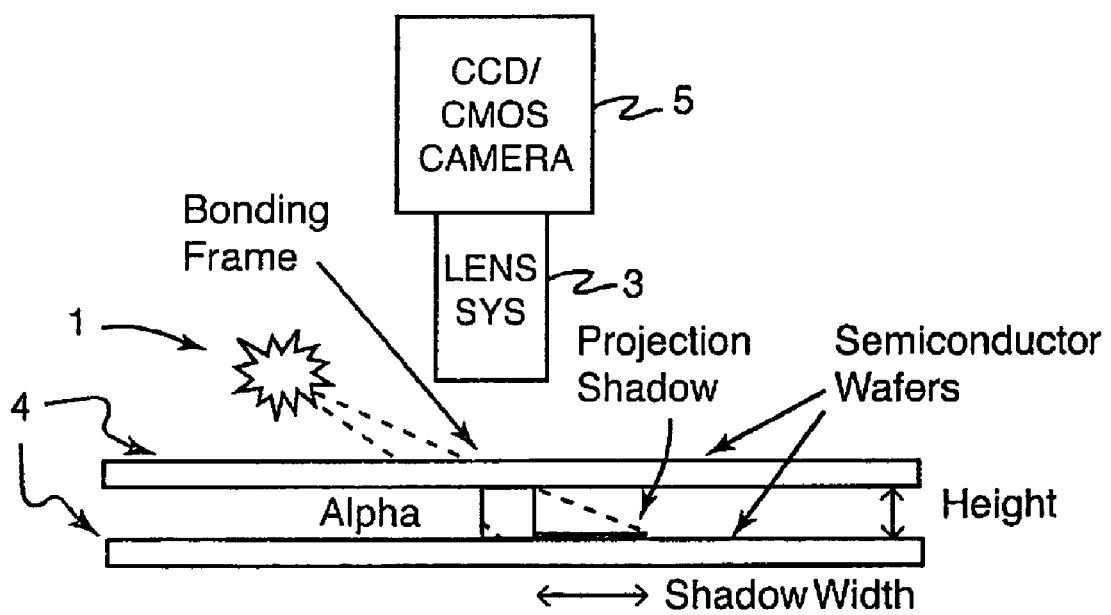
FIG. 8 shows an extension of the third example embodiment in accordance with the invention.

An extension of the third example embodiment, shown in FIG. 8 contemplates capturing a plurality of images with dark field lighting to deduce height information associated with a selected structure 4. Because the image is generated using radiation directed to structure 4 at a known angle (i.e., based on the orientation of the source 1) the height of the structure 4 (or a given feature of the structure 4) is measured by measuring the width of the shadows of the given structure or its given feature. More specifically, the height is given by the product of the measured shadow width and the tangent of the known angle of the directed radiation.

Figure 9:
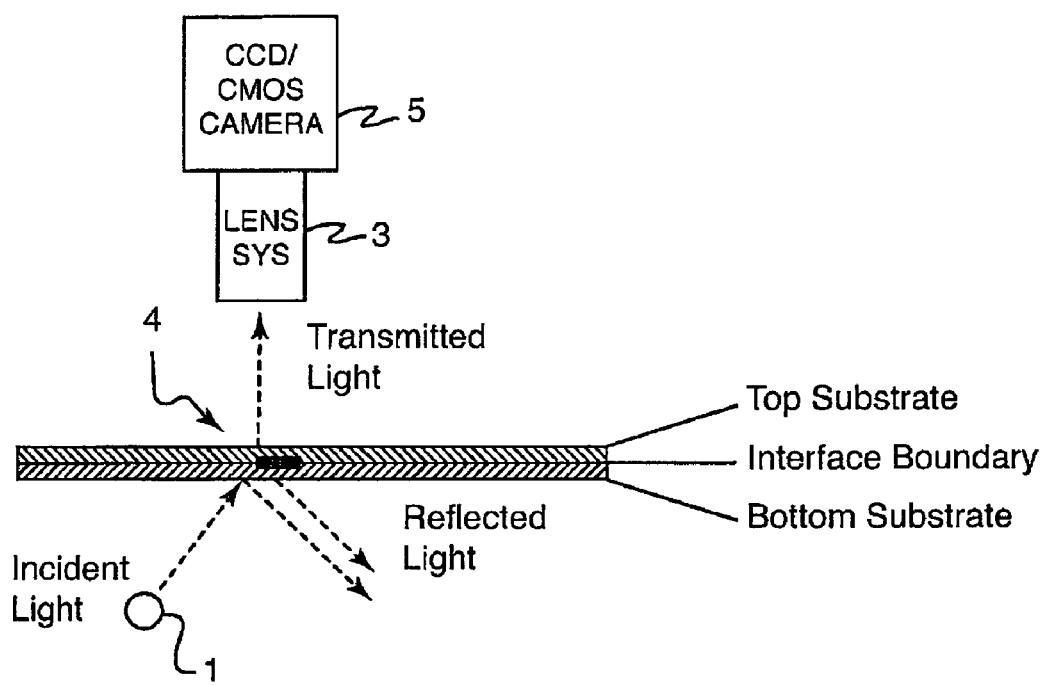
FIG. 9 shows a fourth example embodiment in accordance with the invention.

In a fourth example embodiment, shown in FIG. 9, the radiation source 1 is oriented underneath the to-be-imaged structure 4 so as to direct radiation toward the structure 4, but at an angle from the axis of the lens system 3 and CCD/CMOS camera 5. This orientation is suitable to outline specific directional edges of any given feature located in a transparent or semi-transparent medium, the specific edge direction being determined to be perpendicular to the direction of the light source. This orientation also generates high edge contrast. Similarly, a topside angled radiation source may be used to highlight features and feature textures that may not be visible, or not sufficiently visible, via other methods.

An extension of the fourth example embodiment contemplates capturing a plurality of images with backside light sources shining at different angles to collect all or a substantial variety of directions and construct the multidirectional edge profiles associated with a structure 4.

Figure 10:
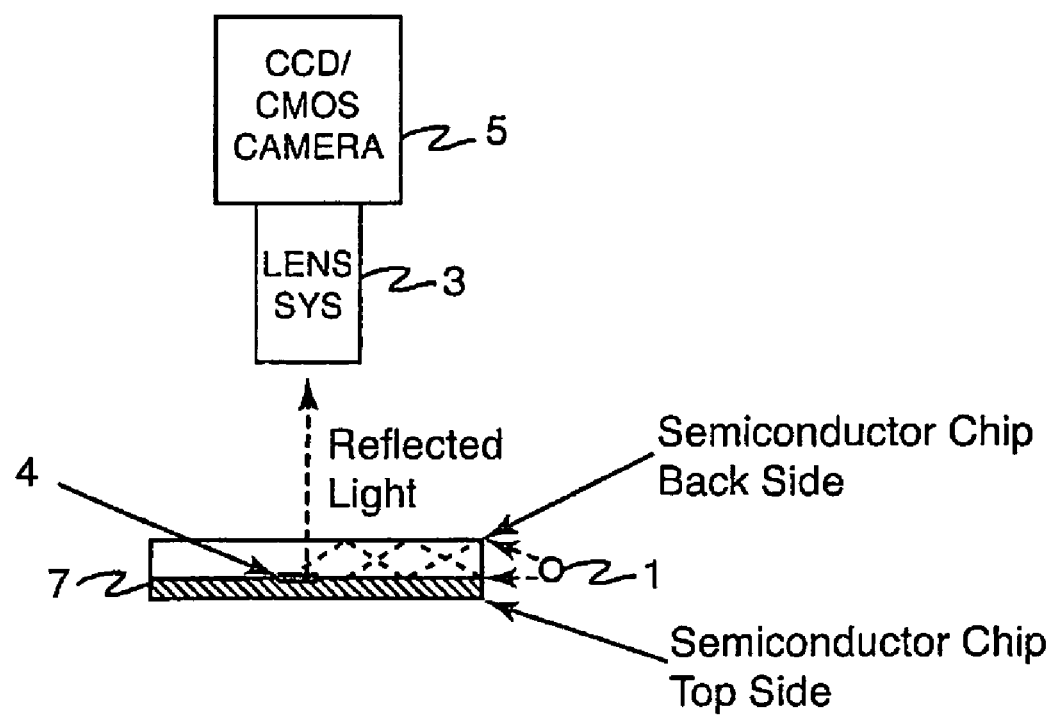
FIG. 10 shows an a fifth example embodiment in accordance with the invention.

In a fifth example embodiment, shown in FIG. 10, the radiation source 1 is oriented to shine precisely perpendicular to the edge of the surface of a semiconductor substrate 7. So delivered, the radiation is retained in the material by total internal reflection, provided that the angle of incidence is less than the critical angle for that material. However, whenever such radiation encounters a feature (e.g., the structure 4) on or at one of the surfaces providing such internal reflection, the radiation will tend to be directed out of the substrate, e.g., from back side of the chip for capture by the lens system 3 and imaging by the CCD/CMOS camera 5. Here, the radiation source 1 typically is a solid state source, preferably a one dimensional array of solid state emitting devices—such as, e.g., LEDs/VCSELs—radiating either through a lens array or through a linearly-arranged fiber optic light guide. This orientation has advantages, including, for example, that it enables provision of enhanced visual contrast of structures disposed inside a semiconductor device, including defects. In practice, absorption of the radiation tends to limit the penetration of the incident light to up to a few millimeters (see Table 2, above for example penetrations into silicon associated with various wavelengths). Even so, when this orientation may be applied, it generally provides useful images of back side device structures, including, as examples, circuitry, cracks, voids and particulate defects embedded within diced semiconductor chips.

Figure 11:
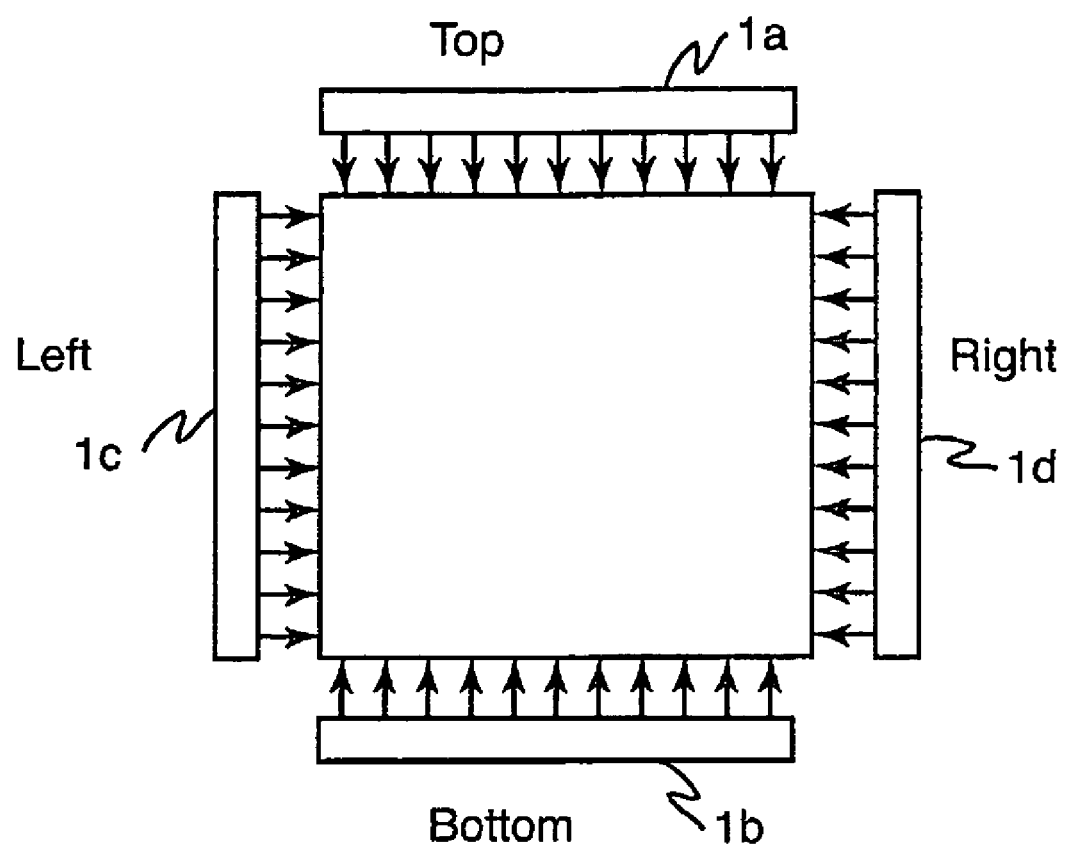
FIG. 11 shows an extension of the fifth example embodiment in accordance with the invention.

An extension of the fifth embodiment, as shown in FIG. 11, contemplates employ of a plurality of radiation sources 1*a*-1*d,* each in an orientation described by the fifth embodiment. More specifically, as illustrated, this extension contemplates employ of four radiation sources, one for each dicing direction (top, bottom, left, right), so as, e.g., to outline directional features embedded within diced semiconductor chips. It is understood that more or less than four sources may be used without departing from the principles of the invention.

Other example embodiments of the invention include, but are not limited to one or more LEDs arrays, or other solid-state radiation source(s):

Irradiating a beam splitter in a through-the-lens lighting system directly (i.e., absent a fiber optic light guide).

Providing top light irradiation in either a "ring" or "dome" configuration.

Providing "ring" or "dome" irradiation via a fiber optic ring or dome light guide.

Providing radiation in backlight and/or toplight orientations, via fiber optic light guide.

Providing a variety of selected wavelength(s) or bands of wavelength(s), such that each source radiates a specific wavelength or band Providing a variety of selected wavelength(s) or bands of wavelength(s), such that each source radiates a specific wavelength or band and each source is subject to individual control, including, as examples, control one or more of: radiating at selected time(s), for selected duration(s), at selected intensities, with selectable collimation, with selected pulse duty cycles, etc. To illustrate, a plurality of arrays may be provided, pairs of which provides distinct, narrow band of wavelengths about a center wavelength, one collimated and the other not collimated, and such that the each array may be sequentially, simultaneously or otherwise powered with respect to any other array(s), such power being for respective time duration(s), or continuing, or in pulse modes of selected duty cycle, so as to enable gathering of various responses of a structure to such applied radiation(s) and with that information (and, preferably, processing thereof), imaging, inspecting or otherwise analyzing the structure, including as to relevant conditions and/or defects.

Still other example embodiments of the invention include, but are not limited to:

Providing fiber-optics in image acquisition

Providing pulsed illumination with synchronized image capture (e.g., synchronizing the camera's shutter or other gating component, of the camera or otherwise).

Providing enhanced high-intensity radiation in, e.g., a through-lighting orientation, such as by super high intensity radiation, preferably pulsed, from one or more LED arrays, in one of more selected bands Solid state sources, such as LEDs, have various characteristics, including some advantages, including:

As compared to bulbs, solid state sources tend to have a direct cost advantage.

Elimination of filters, e.g., IR band pass filters as in FIG. 1 are eliminated because LEDs and LED-based arrays can be provided that deliver narrow band(s) of wavelength(s), thus indirectly reducing cost of and complexity of implementations.

Readily enable implementations having spectral separation between back and top light sources.

Clear images are promoted as LEDs tend to have narrow band radiation, which tends to preclude certain problems, e.g., chromatic aberration (where rays of different wavelengths bend differently when passing through lenses).

Readily enable collimation or absence of collimation.

Narrow band radiation also results in interference fringes in which bonding defects show up as concentric rings due to constructive and destructive interference.

Backlighting is scalable with LEDs by simply increasing size of array.

LEDs have stable light output—eliminates calibration problems with bulbs.

LEDs have long lifetime (~00000 hours)—no need to replace after only 1000 hours as with bulb.

LEDs are narrow band and do not put additional IR (heat) energy into the inspection target. Heat could damage target.

LED arrays can be used to selectively provide collimation at one or more wavelengths.

LED arrays can be populated with various wavelength specific LEDs so as to provide various wavelengths at selected times, e.g., sequential or simultaneous pulsing at various power and duty cycles.

Optics

The lens system typically is selected based on various factors. Examples of these factors include the field-of-view requirements of the imaging/inspection application and the applicable (selected) radiation source orientation (with examples of same described above). Optics typically are treated with antireflective coatings to reduce reflections in a range of selected wavelengths, e.g., those centered on 1070 nm. One example embodiment, with particular application to the first example embodiment described above with reference to FIG. 5, uses a zoom lens which provides a field of view ranging from 6 mm to 40 mm. A second example embodiment, with particular application to the second example embodiment described above with reference to FIG. 6, uses a fixed magnification lens system which provides a field of view of 4 mm, and has both a beam splitter and an input port to accommodate a fiber optic light guide directing radiation from a source. Focus and zoom (if applicable) may be set either/both manually (e.g., by turning a dial) or automatically (e.g., by computer control). For applications where dimensional measurement is required, a telecentric lens may also be used.

Using optics selected for proper magnification and coated for maximum transmission at selected wavelength(s) (e.g., wavelength(s) generally in the 700 nm-3000 nm long visible red to near infrared spectrums, or more specific band(s), e.g., centered on 1070 nm, or centered on 1200 nm or in any of various bands, such as 1050-1200 nm, 1050-1300 nm, or 1000-1300 nm wavelength range), enables the use of high resolution CCD/CMOS imaging devices, e.g., near the upper wavelength limits of their spectral sensitivity.

Imaging

Example embodiments in accordance with this invention employ of a high-sensitivity cameras based on or using CCD/CMOS imaging device(s). CCD/CMOS imaging technologies are substantially mature, particularly relative to some infrared camera technologies, such as those based on arrays of certain gallium arsenide detectors or microbolometers. This maturity translates into various advantages for CCD/CMOS imaging devices and the cameras based thereon, particularly as compared to cameras specific to infrared imaging:

Sensor density: CCD/CMOS cameras are commercially available with up to 8 million pixels (compared to typical infrared cameras which typically have as few as 0.25 million pixels).

Standardized electrical interfaces: CCD/CMOS cameras are commonly available with standard electrical interfaces to frame grabbers, or to flexible high-speed bus architectures, such as IEEE 1492, USB-2, or 100-Base-T.

Cost: CCD/CMOS cameras are significantly less expensive than such infrared cameras (by as much as an order of magnitude).

Noise: CCD/CMOS cameras may have various noise performance (e.g., cameras using scientific-grade solid state imaging devices tend to have superior signal to noise ratios and, generally, relatively low noise characteristics). For those cameras using imaging devices where noise may nevertheless be an issue, the noise may be readily and relatively inexpensively reduced by cooling, e.g., such as through Peltier cooling assemblies.

The use of CCD/CMOS imaging devices is enabled by the use of selected radiation wavelength(s). The radiation wavelengths typically are selected based, among other things on the spectral response of the imaging devices. Generally, particularly for through-substrate orientations, radiation in infrared band may be employed which radiation typically corresponds to significantly diminished sensitivity in semiconductor-based imaging devices, e.g., silicon-based CCDs and CMOS sensors. In a general embodiment in accordance with the invention, tools and processes are provided that exclude (or substantially exclude) radiation wavelengths—other than those of the selected infrared wavelength(s) or band(s)—from the imaging device, such exclusion being maintained at least during for time period(s) associated with imaging using the selected wavelengths. In so doing, the relative insensitivity of the imaging devices is overcome That is, absent wavelengths to which the CCD/CMOS imaging device is more responsive, the imaging device responds only to the narrow band of selected wavelengths and the images reflects such response. Preferably, the signal levels for such imaging are brought up to a measurable level using various approaches, such approaches including, as examples, opening the lens aperture, increasing exposure time, increasing electronic gain, by digitally averaging multiple acquired images, or using other techniques to expose that may be known in the art.

In another general embodiment in accordance with this invention, tools and processes are provided which recognize and respond to the quantum efficiencies and other physical properties of solid state imaging devices. Such tools and processes preferably respond to and result from coordination of various facts and factors, including:

(a) the particular, to-be-imaged semiconductor structure has known or determined semiconductor materials (and associated band-gap energy or energies) and may have features (including conditions and defects) of known or determined parameters, including as to typical size(s), shape(s) and location(s);

(b) radiation wavelength(s) or band(s) of wavelength(s) are selected based on such materials, energies, and parameters, as well as the orientation of the radiation source and subject to the spectral response of the imaging device;

(c) one or more radiation sources are selected and oriented, which radiation sources are enabled to provide the selected wavelength(s) and to deliver the radiation at appropriate orientations (e.g., angles and locations, including from the back side of the structure) relative to the semiconductor structure, as well as, preferably, to control radiation characteristics (including as to intensity, collimation, lack of collimation, pulsing, etc.);

(d) a lens system is selected so as to transmit the selected wavelengths to, and form the images on, the imaging device which selection preferably matches the lens' image-forming capabilities with the imaging device's image-capture capabilities (e.g., the lens is able to resolve features of size equal to, or less than, the feature sizes that the imaging device resolves), so as to properly image the structure as to its relevant feature(s), including conditions and defects; and (e) one or more solid state imaging device(s) are employed that are able to properly capture an image of the structure's relevant features (e.g., conditions and defects), at least one of which imaging devices, among other attributes, has (i) sufficient sensitivity to the selected wavelength(s) to capture the image, provided proper delivery of the radiation is maintained and (ii) sensor cell size and number sufficient to resolve the to-be-imaged imaged structure and its relevant features.

In this general embodiment, when imaging based on a radiation orientation that directs the selected wavelength(s) to the back side of the structure (e.g., for through-substrate imaging), the radiation source preferably provides infrared wavelength(s) that are long enough to be transmitted entirely through the to-be-imaged structure. However, such wavelengths should yet be short enough to enable imaging of the structure and its relevant features, including the various relevant conditions and defects that may be driving the imaging. Principles of physics generally dictate that, to image a device having a relevant dimension "x," the wavelength employed should be "½x" and, preferably, even smaller. In selecting the wavelength(s), this general embodiment contemplates coordination between these two factors, which factors may at times tend to push in different directions (e.g., longer wavelengths to pass through the substrate but shorter wavelengths so as to detect and properly image the structure as to its relevant features).

Moreover, in this general embodiment, the radiation source(s) preferably (i) provides the selected wavelengths (e.g., at appropriate intensities, for sufficient durations, at proper duty cycles) so as to enable the imaging device(s) to capture the image based on the selected wavelengths, i.e., despite the device's relative insensitivity to such wavelengths, while (ii) excluding all (or substantially all) other wavelengths, so that an imaging device's sensor cells are not electrically saturated by such other wavelengths.

Use of CCD/CMOS tends to provide various advantages, with examples including:

Cost advantage

Enhanced flexibility in selection of resolution and pixel sizes (e.g., scientific-grade vs mainstream), such that tools and processes may render detail and "big picture" in same view. More information tends to be collected in one snapshot, which simplifies image analysis.

Improved data rates

CCD/CMOS cameras are mainstream and mature.

Image Enhancement

The images captured by the CCD/CMOS camera in the example embodiments may be enhanced using one or more of various digital image processing techniques. Examples of these techniques include:

Dust removal:—Small particles of dust on the surface of a wafer show up as dark spots in the image, typically very dark spots. The impact of these spots to subsequent image enhancement algorithms and to subjective quality judgments may be reduced by thresholding the image. To do so, all pixels with values less than the threshold are set to the threshold value. This threshold may be variously determined, including empirically. In any case, the threshold is determined so that, in application, it reduces the impact of dust in the image, while having either no (or a non-substantial) impact on the image otherwise. A reasonable threshold setting may be obtained by first computing the mean $$\bar{p} = \frac{1}{N} \sum_{j=1}^{N} p_j$$

and standard deviation $$\sigma = \sqrt{\frac{1}{N-1} \sum_{j=1}^{N} (p_j - \bar{p})^2}$$

of the image pixels. The threshold may then be defined as $$t = \bar{p} - 4\sigma$$

Shading Correction:—The result of non-planar illumination and distortion in the optics train leads to images that tend to be darker near the edges relative to the center. Shading correction is applied to correct this problem and, in so doing, facilitate qualitative and quantitative comparisons between regions of the image that may be illuminated at different levels. Shading correction entails taking a calibration image using a uniform background, with the illumination power set so that the brightest portion of the image (near the center) almost, but does not quite saturate the image. To perform shading correction of subsequent images, each pixel of a raw acquired image is corrected by dividing by the value of the corresponding pixel of the calibration image. This results in an array of pixels in the range [0 . . . 1], which may be renormalized to fit in the more standard pixel range [0 . . . 255] or any other range appropriate to downstream processing.

Scratch removal:—The surfaces of unpolished wafers are often marred by scratches (e.g., horizontal, multi-directional, etc.). Scratches tend to add periodic oriented noise to the digital images obtained with a CCD/CMOS camera. Moreover, scratches interfere with standard computer vision techniques, such as template matching, edge detection, and connectivity analysis, as well as with a human operator's ability to inspect for defects. Therefore it is expedient to digitally remove this oriented noise.

Because this noise is a strong oriented signal in Fourier space, the removal algorithm (i) transforms the implicated image into the Fourier domain by use of the Fast Fourier Transform, (ii) analyzes the transformed image to detect oriented noise, (iii) subtracts a Gabor filtered approximation of the oriented noise, and finally (iv) converts the result back to the image domain via the inverse Fourier transform.

Contrast enhancement:—This image processing algorithm is a form of the well-known histogram equalization technique, in which pixel values are globally remapped according to a "stretching" function. First, the minimum and maximum grey levels are computed. These computed levels are used to remap the original pixel values according to the formula:

$$n_{x,y} = \frac{(2^{bits} - 1)(p_{x,y} - (\min(p) + a))}{(\max(p) - b) - (\min(p) + a)}$$

This function has the effect of linearly stretching the histogram over the complete dynamic range ($0 \ldots 2^{bits} - 1$) of a pixel represented with a number of bits equal to bits. In an example embodiment according to this invention 8 bits per pixel are used; however, it is understood that other bit values may be used without departing from the principles of the invention. The parameters a and b (nominally set to 0) control the dark level and bright level of the histogram. Larger values of a cause the histogram to be stretched more while one or more values of p to be merged into a single value of n. Larger values of b also increase the degree of histogram stretching, i.e., by causing one or more values of p to be merged into a single value of n.

Other pixel transformation functions may also be used without departing from the principles of the invention. As an example, the following function may be used:

$$p_{max} = \bar{p} + c\sigma$$

$$p_{min} = \bar{p} - d\sigma$$

$$n_{x,y} = \frac{(2^{bits} - 1)(p_{x,y} - p_{min})}{p_{max} - p_{min}}$$

In this case, c and d define the upper and lower bounds of the stretched histogram.

Combining images:—Images of the same field of view taken using different radiation sources having different orientations (e.g., toplight, backlight or sidelight) generally emphasize different sets of physical features. Two or more of these images may be merged together in a number of different ways. Examples include:

The pixels in pairs of images may be subtracted to yield a set of differential images. This method is particularly effective when the top semiconductor substrate is unpolished, allowing substantial reduction in signal noise based in the backlight image from the information contained in the top light reflected image.

The pixels in selected three images may be used to represent color channels, e.g., in an RGB image Individual images may be analyzed independently for features that are robustly detectable under each illumination scheme. Measurements may be made between features detected in one image to features in another image.

Deconvolution:—Deconvolution is the process of undoing the smearing in a data set that has occurred under the influence of a known response function, for example, because of the known effect of a less-than perfect measuring apparatus. This definition comes from definition from: Press, W., Teukolsky, S. A., Vettering, W. T., and Flannery, B. P., 1992, *Numerical Recipes in C The Art of Scientific Computing,* Second Edition (Cambridge: Cambridge University Press).

Deconvolution can be applied to help eliminate blurring effects of the optical or imaging system and can yield improved object resolution.

Wiener filtering—Wiener filtering is similar to deconvolution in the presence of noise. The process is to find an optimal filter, which is applied to the input image before deconvolution to eliminate the deleterious effects of noise. This is a well-known technique described in Press, W., Teukolsky, S. A., Vettering, W. T., and Flannery, B. P., 1992, *Numerical Recipes in C The Art of Scientific Computing*, Second Edition (Cambridge: Cambridge University Press) and Gonzalez, R. C. and Wintz, P., 1987, *Digital Image Processing*, Second Edition (Reading, Mass.: Addison-Wesley Publishing Company).

Figure 12:
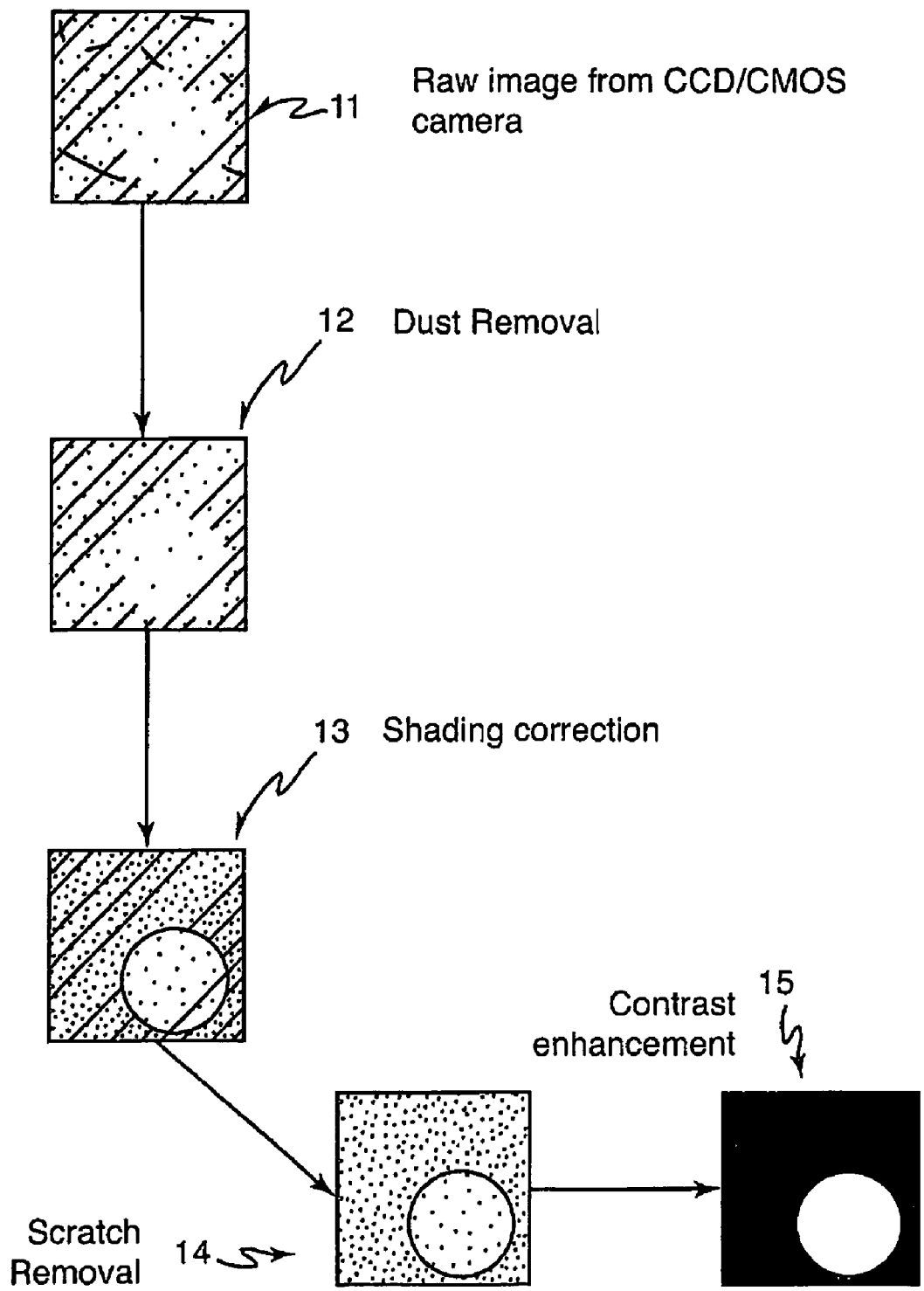
FIG. 12 illustrates an example flow chart of representative image processing operations contemplated to be performed in accordance with this invention.

FIG. 12 illustrates an example flow chart of representative image processing operations contemplated to be performed in accordance with this invention. In step 11, a raw image is captured by a CCD/CMOS camera and made available for image processing. In various example embodiments describe above, such processing is performed using a computer 6, such as a PC. However, it is to be recognized that any one or more image processing algorithms may be implemented other than via a PC, without departing from the principles of the invention. As an example, the algorithms may be provided via electronics and/or software associated with the camera itself (e.g., triggered by selecting a hard or soft button on the camera).

In step 12, dust is removed, as described above or otherwise. In step 13, shading correction is performed, as described above or otherwise. In step 14, scratch removal is performed, as described above or otherwise. In step 15, contrast enhancement is performed, as described above or otherwise.

Application

Figure 13:
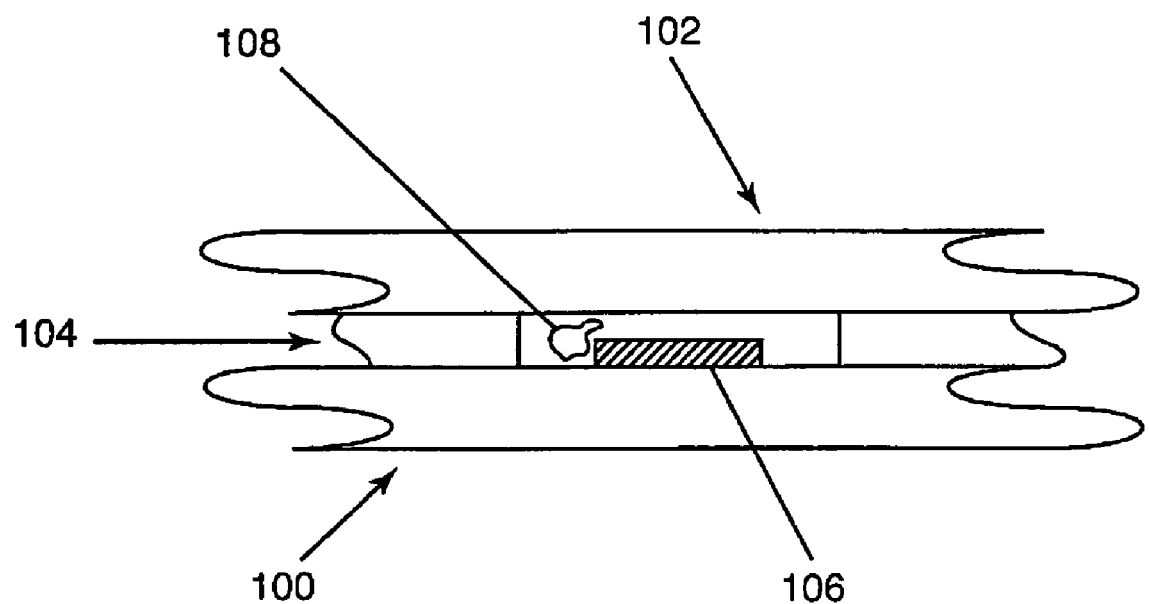
FIG. 13 shows a cutaway side view of a typical MEMs sensor wafer sandwich for imaging and inspection using tools and processes in accordance with the invention.

FIG. 13 shows a cutaway side view of a typical MEMs sensor wafer sandwich. The substrate layer 100 and the cap layer 102 are both made of silicon, which is transparent to wavelengths in the near infrared spectrum (NIR). The bond layer 104 holds the substrate layer 100 and the cap layer 102 together and, depending on the specifics of the wafer construction process, may serve as a hermetic seal to protect devices 106 from the environment. The purpose of the imaging and inspection process is to verify the integrity and consistency of the bond layer 106, including any defects 108 (e.g., here illustrated as a void) that may be disposed therein. These conditions and defects may be identified and measured from digital images captured using tools and processes, according to the invention. To do so, the incident radiation generally will include selected infrared wavelength(s) or band(s), so as to penetrate to the bond layer and any relevant features therein (e.g., the above-described conditions and defects).

Figure 14:
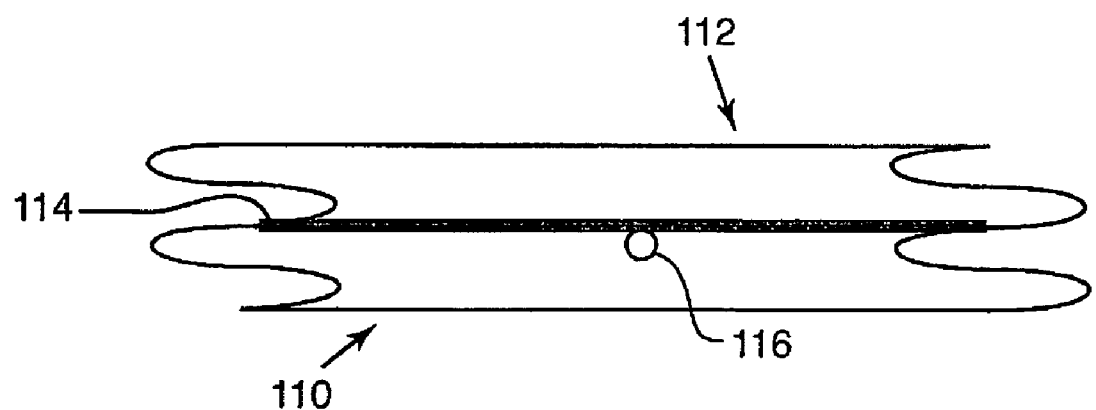
FIG. 14 shows a cutaway side view of a typical fusion bonded wafer sandwich for imaging and inspection using tools and processes in accordance with the invention.

FIG. 14 shows a cutaway side view of a typical fusion bonded, bare wafer sandwich as is typically used in production of Silicon on Insulator (SOI) bare wafers. This structure includes a substrate carrier layer 110, a cap layer 112 and a bond layer 114.

In such structures, uniformity and integrity in the bond layer is generally of importance. As such, presence of particulates, voids or other defects 116 in the bond layer 114, or even slight differences in uniformity are not desirable. Accordingly, relevant features for imaging and inspection including the uniformity condition, as well as any particulate, void or other defects associated with the bond layer 114. Again, such conditions and defects may be identified and measured from digital images captured using tools and processes, according to the invention. To do so, the incident radiation generally will include selected infrared wavelength(s) or band(s), so as to penetrate to the bond layer and to any relevant features therein (e.g., the above-described conditions and defects). In that imaging, subjecting the structure to narrow band IR backlight illumination in the presence of particulates/voids in the bond layer 114, or even slight differences in uniformity therein, will generally result in formation of interference fringes in the image. With a more broadband illumination, such interference fringes (also referred to as ring patterns) tend to appear in the image, with proximity to bond layer defects.

Figure 15:
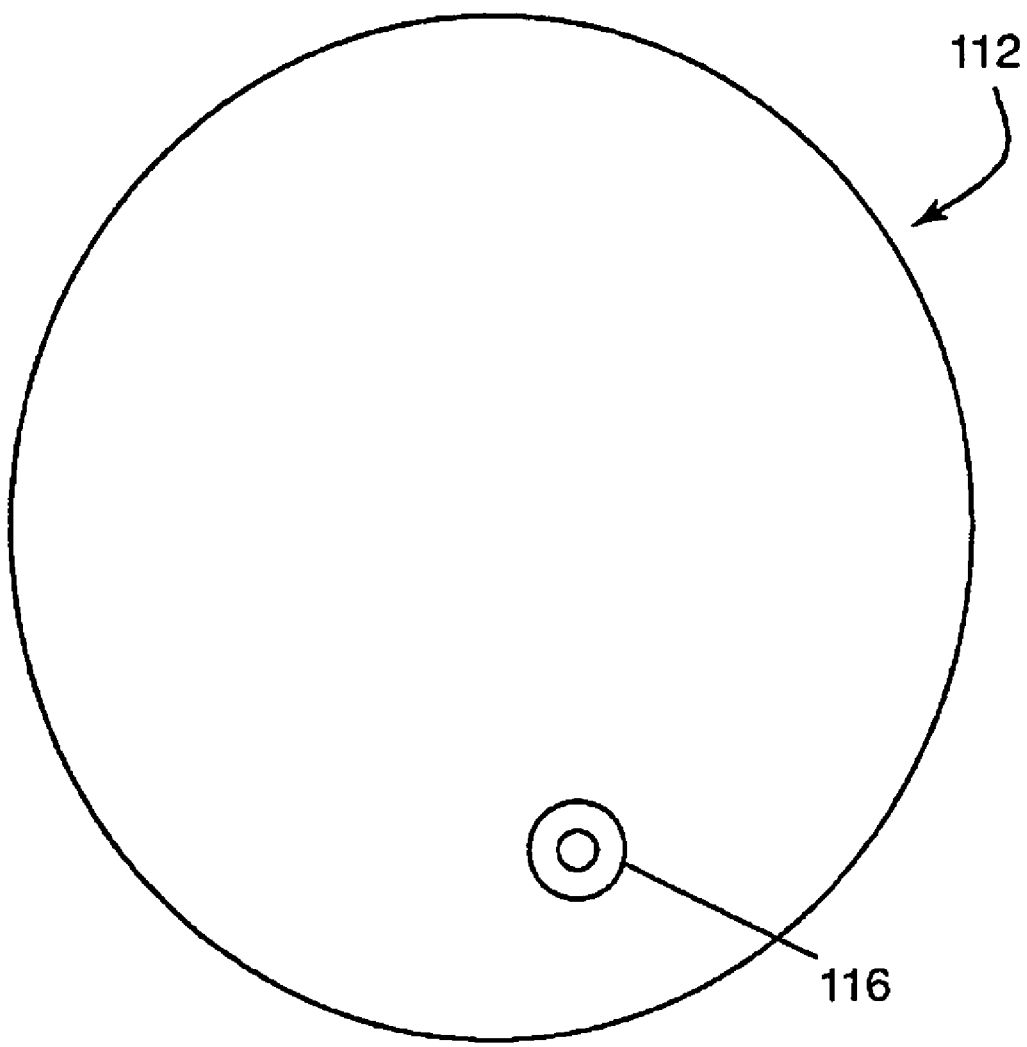
FIG. 15 illustrates representative ring patterns that might typically be formed when imaging a fusion bonded bare wafer using tools and processes in accordance with the invention.

FIG. 15 illustrates a representative ring pattern that might typically be formed when imaging a fusion bonded bare wafer using tools and processes in accordance with the invention. These periodic patterns are readily detected by eye, and may be automatically detected by an algorithm designed to detect such periodic features. The fringes may also be used to estimate the height of internal defects. One full period of an interference fringe (transition from dark to light to dark again) corresponds to a change in distance between bonded materials of 1 wavelength of incident light.

Figure 16:
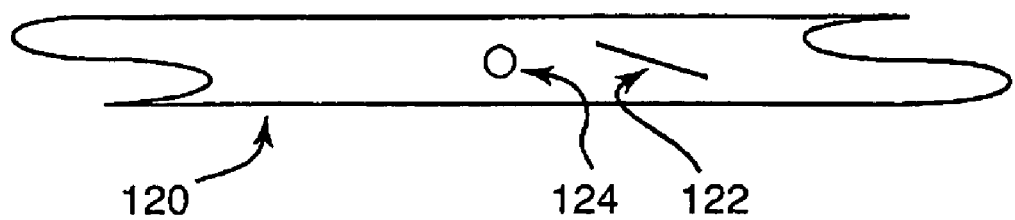
FIG. 16 shows a cutaway side view of a single semiconductor wafer for imaging and inspection using tools and processes in accordance with the invention.

FIG. 16 shows a cutaway side view of a single semiconductor wafer 120, which wafer 120 may be either patterned or non-patterned. Interior to the wafer 120, a crystalline bond is shown to be cleaved, resulting in formation of a micro crack 122. Also interior to the wafer is a void or insertion defect 124. Clearly, neither such defect is desirable (and, being interior to the wafer 120, each such crack or defect may slip detection using conventional imaging and inspection approaches, e.g., with typical pattern, electrical, or surface inspection tools). Moreover, depending on the circuits to be constructed using such wafer 120, even one such micro-crack 122 or defect 124 may result in unacceptably low, and thus, costly yields and/or poor long-term reliability.

Accordingly, relevant features for imaging and inspection in even single wafers include micro-cracks 122 and void, insertion or other defects 124 interior to the wafer 120. Again, such conditions and defects may be identified and measured from digital images captured using tools and processes, according to the invention. To do so, the incident radiation generally will include selected infrared wavelength(s) or band(s), so as to penetrate into the wafer's interior to any of the above-described conditions or defects. By imaging through the wafer 120 at an angle or with infrared backlight, the presence of any such micro-crack or defect may be detected.

Figure 17:
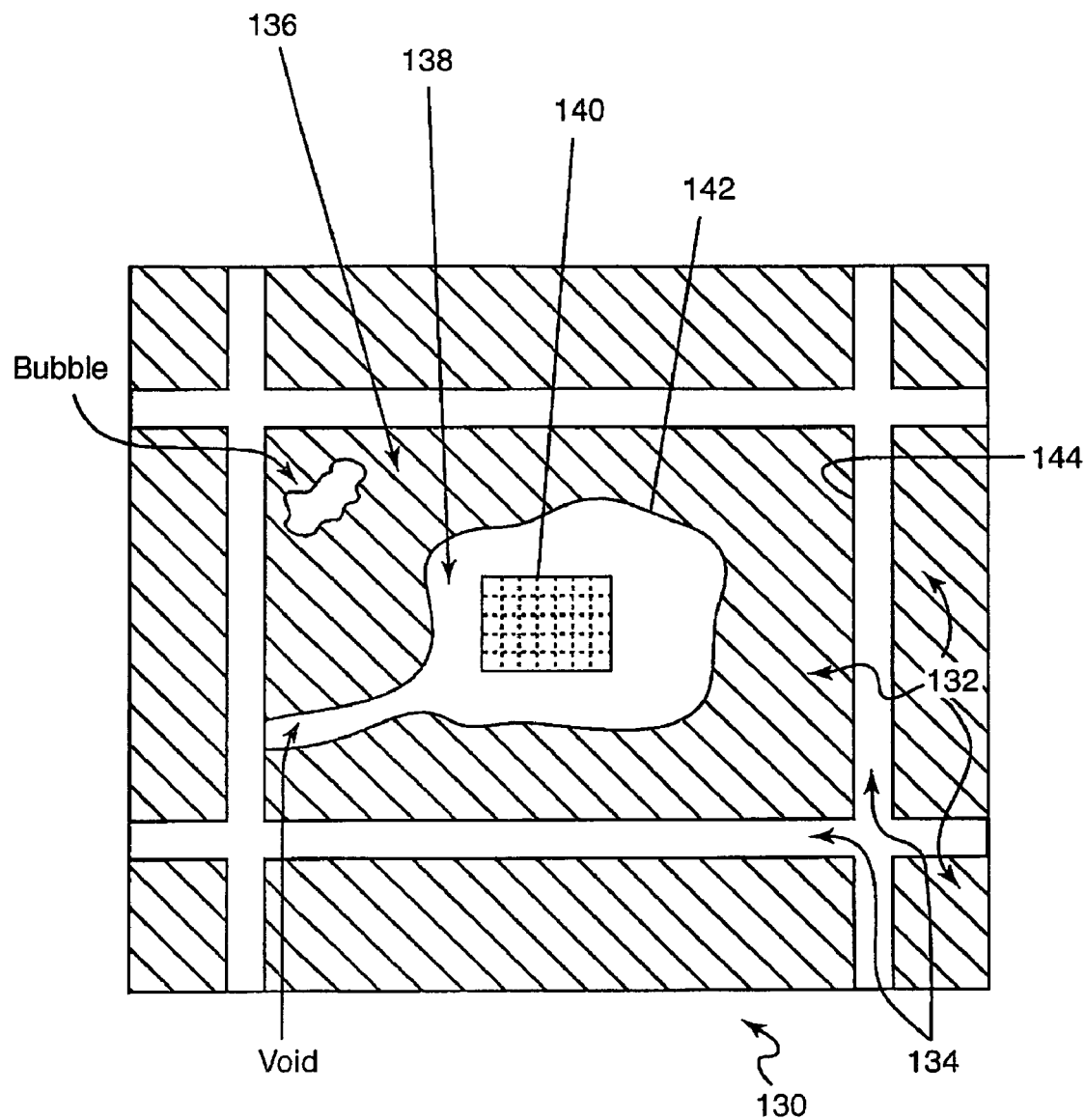
FIG. 17 guides discussion of how various features of a semiconductor device are depicted imaging using tools and processes in accordance with the invention.

FIG. 17 guides discussion of how various features of a semiconductor device are depicted imaging using tools and processes in accordance with the invention. Here, a typical patterned wafer 130 has devices 132 positioned in a regular grid on the wafer's surface. Dicing lines 134 indicate where the wafer 130 will be cut to liberate individual devices 132 for packaging and, prior to such cutting process, such lanes separates the devices 132. In digital imaging, a bond region 136 is recognized (and distinguished) from a "no print" zone 138 surrounding certain active circuitry 140 of the device 132. That recognition is achieved based on variation in the intensity of light reaching the camera at that position, relative to other positions. Since the bonding material attenuates light more than the air filling a void region, the bond region 136 (demarcated by inner boundary 142 and outer boundary 144) will appear darker in the resulting image. Similarly, the silicon features making up the dicing lines 134 and other surrounding wafer features will appear even darker than the bond region 136.

With reference to FIG. 17, an example process inspecting a typical patterned wafer has the following steps:

Locate the circuitry 140 and/or the device 132 (optionally, use this position to fix the detection of the following features). The circuitry/device 140, 132 may be located by, e.g., a template matching algorithm, such as an algorithm utilizing normalized correlation suffices.

Locate the outer boundary 144 of the bond region 136. The outer boundary 144 may be located, e.g., with any of a variety of line detection or "caliper" tools. Such tools find the location of extended straight lines between regions of image contrast.

Locate the inner boundary 142 of the bond region 136. The typically irregular inner boundary may be identified by applying any of a variety of line detection tools, toward finding, e.g., a set of short line segments that approximate an inner boundary contour. Greater approximation accuracy may be achieved by increasing the number of detectors used.

Compute the distance from each point along the bond region's inner boundary 142 to its outer boundary 144.

Locate all voids in the bond region. Voids may be identified by using connectivity analysis. Connectivity analysis separates the foreground from background by considering foreground to be all image components with a grey scale value larger than a threshold. The threshold is determined empirically and varies depending on application, optics, lighting, and imaging.

Figure 18:
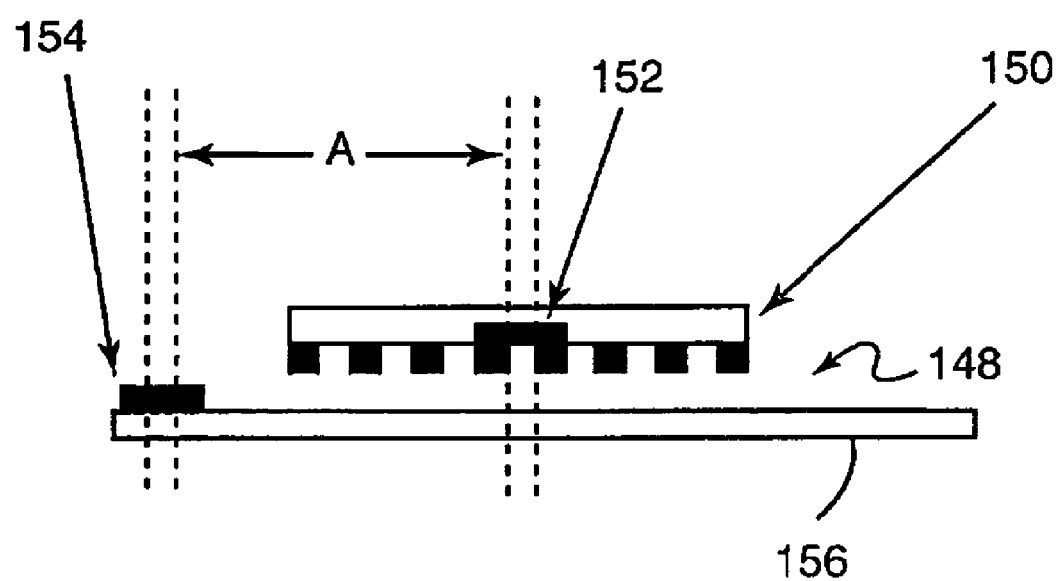
FIG. 18 shows a cutaway side view of a semiconductor package application for imaging and inspection using tools and processes in accordance with the invention.

FIG. 18 shows a cutaway side view of a semiconductor package application 148. Flip chip devices 150 are typically bare dies placed upside down upon a piece of interposer material, typically glass based or organic based. Placement accuracy can be ascertained by imaging and inspecting the position of an on-chip alignment target 152 (e.g., imaging through the chip) relative to the position of an alignment target 154 on the substrate 156. In this FIG. 18 the respective alignment targets are shown to have a displacement Δ.

Figure 19:
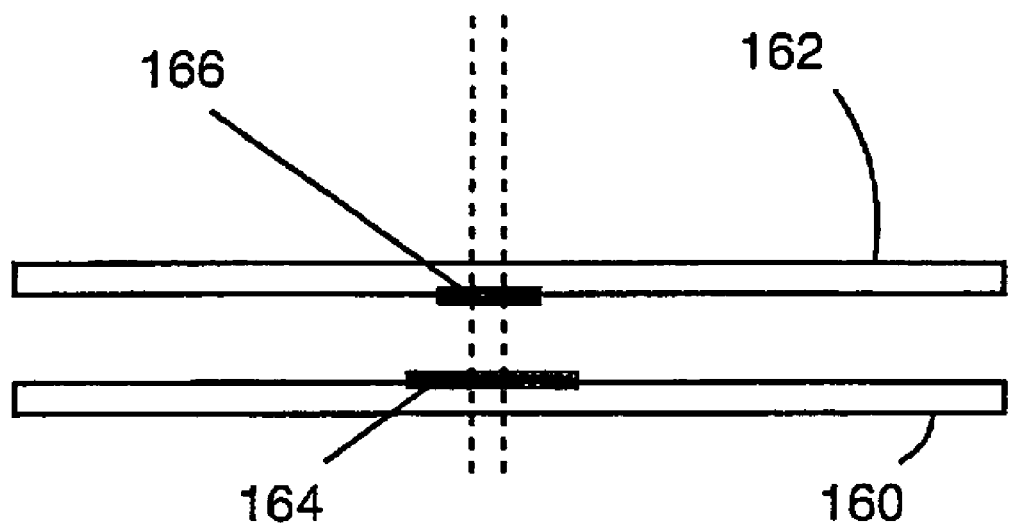
FIG. 19 shows a cutaway side view of two wafers being aligned and bonded.

A similar application arises when two wafers are to be aligned and then bonded. As shown in FIG. 19, a lower substrate 160 is positioned underneath a cap substrate 162. Substrates 160 and 162 have respective alignment targets 164 and 166. Placement accuracy can be ascertained by imaging and inspecting the relative positions of such on-substrate alignment targets 164, 166 (e.g., imaging through the cap substrate to do so). In this FIG. 19, the respective alignment targets 164, 166 are shown to be aligned.

Application of the principles of the invention to image and inspect is viable for, but not limited to, a number of semiconductor structures. These structures include, as examples: micro electromechanical devices, CCDs, CMOS sensors, other sensors, electro-optical components, semiconductors with mirrors.

These operations generally may be performed using well-known computer vision techniques. A number of computer vision software packages are commercially available (for example, MVTec's Halcon, or Intel's Integrated Performance Primitives (IPP)) that provide a rich set of software tools.

Persons skilled in the art will recognize that many modifications and variations are possible in the details, materials, and arrangements of the parts and actions which have been described and illustrated in order to explain the nature of this invention and that such modifications and variations do not depart from the spirit and scope of the teachings and claims contained therein.

What is claimed:

1. A system for imaging subsurface features of a target object comprising a semiconductor-based material having first and second surfaces, and a subsurface therebetween, the system comprising:
   a solid-state sensor having an array of pixels and a sufficient quantum efficiency for wavelengths between about 750 nm and about 3000 nm to image subsurface structures or structure features in the semiconductor material illuminated by radiation wavelength between about 750 nm and about 3000 nm, when a portion of the radiation that illuminated the subsurface is incident on the image sensor; and
   a solid-state radiation source operable with a radiation output in the aforesaid wavelength range, wherein the radiation source and the image sensor are arranged in the system so that the output radiation penetrates through material forming the first and/or second surface and into underlying subsurface material, and is thereafter directed to the sensor.

2. A system as in claim 1, wherein the solid state radiation source comprises one or more high-density arrays of light-emitting diodes, such an array providing for control over and selected variations of, one or more of (i) collimation of a selected first and/or second wavelength and/or (ii) intensity and/or (iii) duty cycle.

3. A system as in claim 2, wherein one or more of the high-density arrays of light-emitting diodes is controllable as to collimation of radiation and disposed relative to the work object so as to provide for selected incident angle of the radiation.

4. A system as in claim 1, further comprising selected one or more additional radiation sources, so as to support a selected combination of front side, backside, side and/or dark field irradiation of the work object.

5. A system as in claim 1, further comprising an image processing mechanism, which mechanism supports one or more of stretching the region of interest, identifying edges and features in the image, and automatically inspecting the target object.

6. A system as in claim 5, wherein the image processing mechanism provides for measuring height of a semiconductor structure or feature disposed between two layers of semiconductor materials.

7. A system as in claim 1, wherein the first solid state radiation source provides radiation at a selected combination of orientation, collimation, wavelength, duty cycle, coherence and intensity sufficient to enable detection of defects associated with a target object that includes direct fusion bonded semiconductor materials.

8. A system as in claim 1, wherein the imaging device captures an image of semiconductor structure that comprises at least one alignment target.

9. A system as in claim 1, wherein the imaging system provides for capturing an image representing the depth or z location of a buried defect, like a crack, dislocation or void, whereby such depth or z location is measured.

10. The system of claim 1 wherein the radiation source and image sensor are arranged to allow placement of the target object between the radiation source and the image sensor so that light passes directly through the target object to reach the sensor.

11. The system of claim 10 wherein the light source is operable to output a wavelength range comprising about 1050 nm to about 1300 nm.

12. The system of claim 1 wherein the radiation source is disposed so as to allow placement of the radiation source on the same side of the target object as the image sensor so that radiation passes through the target object and is reflected back to the sensor, again through the target object.

13. The system of claim 12 wherein the light source is operable to output a wavelength range comprising about 1050 nm to about 1300 nm.

14. The system of claim 12 wherein one of the first or second surfaces comprises a reflective material that reflects the radiation penetrating the subsurface back through the subsurface to the image sensor.

15. The system of claim 1 wherein the light source is operable to output a wavelength range comprising about 1050 nm to about 1300 nm.

16. The system of claim 1 wherein the light source is operable to output radiation of at least two different wavelengths within the range.

17. The system of claim 1 wherein the system provides for imaging a silicon-based semiconductor material.

18. The system of claim 1 wherein the target object comprises a semiconductor device with subsurface semiconductor structures having features to be imaged.

19. The system of claim 1 wherein the subsurface includes a structure comprising the semiconductor material to be imaged.

20. A process for an inspection system as in claim 19, further comprising operating the solid state radiation source so that, when imaging using wavelengths transmissive of the semiconductor material, other wavelengths are substantially excluded, whereby the image sensor images the target object responsive to the selected, transmissive wavelengths.

21. The system of claim 1 wherein the subsurface comprises two or more layers of semiconductor materials to be imaged for structures or features.

22. A system as in claim 1, further comprising a second solid state radiation source and wherein at least one of the first or second solid state radiation sources provides radiation at a selected combination of orientation, collimation, wavelength, duty cycle, coherence and intensity sufficient to enable detection of defects associated with a target object that includes direct fusion bonded semiconductor materials.

23. A system as in claim 1, wherein the solid-state radiation source comprises one or more high-density arrays of light-emitting diodes configured to vary a collimation of a selected wavelength of radiation.

24. A process for imaging a target object comprising a semiconductor-based material having first and second surfaces, and a subsurface therebetween, the process comprising:
  providing a solid-state sensor having an array of pixels and a sufficient quantum efficiency for wavelengths between about 750 nm and about 3000 nm to image subsurface structures or structure features in the semiconductor material illuminated by a radiation wavelength between about 750 nm and about 3000 nm, when a portion of the radiation that illuminated the subsurface is incident on the image sensor; and
  providing a solid-state radiation source operable with a radiation output in the aforesaid wavelength range; and arranging the radiation source and the image sensor in the system so that the output radiation penetrates through material forming the first and/or second surface and into underlying subsurface material, and is thereafter directed to the sensor.

25. The process of claim 24 further comprising providing for capturing an image representative of subsurface semiconductor structure features that comprise crystal defects, cracks, insertions or voids.

26. A process for an inspection system as in claim 24, wherein the radiation source comprises one or more high-density arrays of light-emitting diodes, such one or more arrays providing for control over and selected variations of, one or a combination of two or all of, (i) collimation of the selected first and/or second radiation wavelengths and/or (ii) intensity and/or (iii) duty cycle.

27. A process for an inspection system as in claim 24, further comprising operating the system using one or more radiation wavelength(s) or band(s) of wavelength(s) provides wavelength(s) that are both long enough to be transmitted entirely through the structure and short enough to enable imaging of the features.

28. The process of claim 24 further comprising placing the target object into the system so that it is arranged for radiation to pass through it to the image sensor, in the manner said, and outputting radiation so that it penetrates through the first and/or second surface and into the subsurface and is then directed to the sensor.

29. The process of claim 28 wherein the target object comprises a MEMs device, and further comprising the step of operating the radiation source and image sensor to inspect the device for defects.

30. The process of claim 28 wherein the target object comprises one or more bonded layers, and further comprising the step of operating the radiation source and image sensor to inspect the target object, assessing for defects at a bond layer interface.

31. The process of claim 24 wherein the radiation source and image sensor are arranged to allow placement of the target object between the radiation source and the image sensor so that light passes directly through the subsurface to reach the sensor.

32. The process of claim 31 wherein the light source is operable to output a wavelength range comprising about 1050 nm to about 1300 nm.

33. The process of claim 24 wherein the radiation source is disposed so as to allow placement of the radiation source on about the same side of the target object as the image sensor so that radiation penetrates through the subsurface and is reflected back to the sensor, again through the subsurface.

34. The process of claim 33 wherein the light source is operable to output a wavelength range comprising about 1050 nm to about 1300 nm.

35. The process of claim 33 wherein one of the first or second surfaces comprises a reflective material that reflects the radiation penetrating the subsurface back through the subsurface to the image sensor.

36. The process of claim 35 wherein the target object comprises a semiconductor device and a metallic layer in the device comprises the reflective material.

37. The process of claim 24 wherein the light source is operable to output a wavelength range comprising about 1050 nm to about 1300 nm.

38. A process as in claim 24, wherein the solid-state radiation source comprises one or more high-density arrays of light-emitting diodes configured to vary a collimation of a selected wavelength of radiation.

* * * * *